US007879822B2

(12) United States Patent
Dagan et al.

(10) Patent No.: US 7,879,822 B2
(45) Date of Patent: Feb. 1, 2011

(54) STABILIZED SULFORAPHANE

(75) Inventors: Ido Dov Dagan, Asheville, NC (US); Albert Roger Frisbee, Hendersonville, NC (US); Peter Wyatt Newsome, Horse Shoe, NC (US); Michel Pierre Baudet, Durham, NC (US)

(73) Assignee: Pharmagra Labs, Inc., Brevard, NC (US)

( * ) Notice: Subject to any disclaimer, the term of this patent is extended or adjusted under 35 U.S.C. 154(b) by 293 days.

(21) Appl. No.: 12/009,874

(22) Filed: Jan. 23, 2008

(65) Prior Publication Data

US 2008/0176942 A1 Jul. 24, 2008

Related U.S. Application Data

(60) Provisional application No. 60/881,875, filed on Jan. 23, 2007.

(51) Int. Cl.
*A61K 31/26* (2006.01)
*A61K 31/724* (2006.01)

(52) U.S. Cl. ..................... 514/58; 514/514
(58) Field of Classification Search ............. None
See application file for complete search history.

(56) References Cited

U.S. PATENT DOCUMENTS

| | | | |
|---|---|---|---|
| 5,411,986 A | 5/1995 | Cho et al. | 514/514 |
| 5,589,504 A | 12/1996 | Danneberg et al. | 514/456 |
| RE36,784 E | 7/2000 | Cho et al. | 424/94.1 |
| 6,117,429 A | 9/2000 | Bucci | 424/195.1 |
| 6,433,011 B1 | 8/2002 | Chung et al. | 514/514 |
| 6,511,675 B2 | 1/2003 | Siddiqui et al. | 424/439 |
| 6,558,723 B2 | 5/2003 | Ekanayake et al. | 426/321 |
| 6,699,849 B1 | 3/2004 | Loftsson et al. | 514/58 |
| 6,716,827 B1 | 4/2004 | Roselli et al. | 514/58 |
| 6,737,441 B2 | 5/2004 | Fahey | 514/514 |
| 6,812,248 B2 | 11/2004 | Zhang et al. | 514/514 |
| 6,984,632 B1 | 1/2006 | Mascagni et al. | 514/58 |
| 2001/0034333 A1 | 10/2001 | Kosak | |
| 2003/0091518 A1 | 5/2003 | Pauly et al. | |
| 2004/0180843 A1 | 9/2004 | Fahey | |
| 2006/0264497 A1 | 11/2006 | Zeligs | |

FOREIGN PATENT DOCUMENTS

| FR | 2 888 235 A1 | 1/2007 |
|---|---|---|
| JP | 2002187842 | * 7/2002 |

OTHER PUBLICATIONS

Machine translation of JP 2002-187842 (2002).*
Hedges, A. "Industrial applications of cyclodextrins" Chem. Rev. (1998) vol. 98, pp. 2035-2044.*
Carlson, D. et al "Glucosinolates in crucifer vegetables . . . " J. Am. Soc. Hort. Sci. (1987) vol. 112, No. 1, pp. 173-178.*

James K. Whitesell et al.; *Asymmetric Synthesis of Chiral Sulfinate Esters and Sulfoxides Synthesis of Sulforaphane*; J. Org. Chem, 1994, 59, pp. 597-601.

P. Pitchen, et al.; *An Efficient Asymmetric Oxidation of Sulfides to Sulfoxides*; J. Am. Chem. Soc. 1984, 106, pp. 8188-8193.

PCT International Preliminary Report on Patentability, date of issuance of report Jul. 28, 2009, date of mailing Aug. 6, 2009, The International Bureau of WIPO, International Application No. PCT/US2008/000832, International Filing Date Jan. 23, 2008, Applicant Pharmagra Labs, Inc. et al.

Xuehong Li, et al., Complexation of allyl isothiocyanate by alpha- and beta-cyclodextrin and its controlled release characteristics, ScienceDirect, Food Chemistry 103 (2007) 461-466. Available online at www.sciencedirect.com.

Yoshio Ohta, et al., Retarding Effects of Cyclodextrins on the Decomposition of Organic Isothiocyanates in an Aqueous Solution, Biosci. Biotechnol. Biochem, 68 (3), 671-675, 2004.

Yoshio Ohta, et al., Effects of Ionized Cyclodextrin on Decomposition of Allyl Isothiocyanate in Alkaline Solutions, Biosci. Biotechnol. Biochem, 68 (2), 433-435, 2004.

Yoshio Ohta, et al., Kinetic and Thermodynamic Analyses of the Cyclodextrin-Allyl Isothiocyanate Inclusion Complex in an Aqueous Solution, Biosci. Biotechnol. Biochem., 63 (7), 190-193, 1999.

European Patent Office, Communication, dated May 6, 2010, with enclosed Supplementary European Search Report, completed Mar. 24, 2010, European Patent Application No. 08724719.3, Pharmagra Labs, Inc.

Graham P. Basten, et al., Sulforaphane and its glutathione conjugate but not sulforaphane nitrile induce UDP-glucuronosyl transferase (UGT1A1) and gluthathione transferase (GSTA1) in cultured cells, Garcinogenesis vol. 23 No. 8 pp. 1399-1404, 2002, Copyright Oxford University Press.

Radomir Pechacek, et al., Decomposition Products of Allyl Isothiocyanate in Aqueous Solutions, J. Agric. Food Chem. 1997, 45, 4584-4588, Copyright 1997 American Chemical Society.

Leslie G. West, et al., Glucoraphanin and 4-Hydroxyglucobrassicin Contents in Seeds of 59 Cultivars of Broccoli, Raab, Kohlrabi, Radish, Cauliflower, Brussels Sprouts, Kale, and Cabbage, J. Argic. Food Chem. 2004, 52, 916-926, Copyright 2004 American Chemical Society, published on Web Jan. 22, 2004.

PCT International Search Report, International Application No. PCT/US08/00832, International Filing Date Jan. 23, 2008, ISR completed May 2, 2008, ISR mailed May 23, 2008.

Schenk, W.A.; Durr, M.; Steinmetz, B.; Adam W.; Saha-Moller, C.R. *Selective Reactions of Metal-Activated Molecules, Proceedings of the Symposium*, 3$^{rd}$ 1998, 245-246.

(Continued)

*Primary Examiner*—Leigh C Maier
(74) *Attorney, Agent, or Firm*—Nelson Mullins Riley & Scarborough, LLP

(57) ABSTRACT

A method of stabilizing sulforaphane is provided. The method includes contacting sulforaphane, or an analog thereof, and a cyclodextrin to form a complex between the sulforaphane, or analog thereof, and the cyclodextrin.

33 Claims, 8 Drawing Sheets

OTHER PUBLICATIONS

Conaway, C.C.; Jiao, D.; Chung, F-L, *Inhibition of rat liver cytochrome P450 isozymes by isothiocyanates and their conjugates: a structure-activity relationship study*, Carcinogenesis vol. 17 No. 11 pp. 2423-2427,1996.

Barcelo, S.; Gardiner, J.M.; Gescher, A.; Chipman, J.K.; *CYP2E1-mediated mechanism of anti-genotoxicity of the broccoli constituent sulforaphane*, Carcinogenesis vol. 17 No. 2 pp. 277-282,1996.

Langouet, S.; Johnson, W.W.; Guillouzo, A.; Guengerich, F.P.; *Detoxication of Aflatoxin B1 as a Model for Carcinogen Metabolism*, In Vitro & Molecular Toxicology, vol. 11, No. 1, pp. 95-101, 1998.

Gamet-Payrastre, .L; Lumeau, S.; Gasc, N.; Cassar, G.; Rollin, P.; Tulliez, J.; *Selective cytostatic and cytotoxic effects of glucosinolates hydrolysis products on human colon cancer cells in vitro*, Anti-Cancer Drugs, vol. 9, pp. 141-148, 1998.

Fei, P.; Matwyshyn, G.A.; Rushmore, T.H.; Kong, A-N.T.; *Transcription Regulation of Rat Glutathione S-Transferase Ya Subunit Gene Expression by Chemopreventive Agents*, Pharmaceutical Research, vol. 13, No. 7, pp. 1043-1048, 1996.

Zhang, Y.; Talalay, P.; *Mechanism of Differential Potencies of Isothiocyanates as Inducers of Anticarcinogenic Phase 2 Enzymes*, Cancer Research 58, pp. 4632-4639, Oct. 15, 1998.

Mahéo, K.; Morel, F.; Langouët, S.; Kramer, H.; Le Ferrec, E.; Ketterer, B.; Guillouzo, A.; *Inhibition of Cytochromes P-450 and Induction of Glutathione S-Transferases by Sulforaphane in Primary Human and Rat Hepatocytes*, Cancer Research 57, pp. 3649-3652, Sep. 1, 1997.

Kassahun, K.; Davis, M.; Hu, P.; Martin, B.; Baillie, T.; *Biotransformation of the Naturally Occurring Isothiocyanate Sulforaphane in the Rat: Identification of Phase I Metabolites and Glutathione Conjugates*, Chem. Res. Toxicol, 1997, 10 pp. 1128-1233.

Posner, G.H.; Cho, C.-G.; Green, J.V.; Zhang, Y.; Talalay, P.; *Design and Synthesis of Bifunctional Isothiocyanate Analogs of Sulforaphane: Correlation between Structure and Potency as Inducers of Anticarcinogenic Detoxication Enzymes*, J. Med. Chem., 1994, 37, pp. 170-178.

Prestera, T.; Holtzclaw, W.D.; Zhang, Y.; Talalay, P.; *Chemical and molecular regulation of enzymes that detoxify carcinogens*, Proc. Natl. Acad. Sci. USA, vol. 90, pp. 2965-2969, Apr. 1993, Medical Sciences.

Zhang, Y.; Talalay, P.; Cho, C.-G.; Posner, G.H.; *A major inducer of anticarcinogenic protective enzymes from broccoli: Isolation and elucidation of structure*, Pro. Natl. Acad. Sci. USA, vol. 89, pp. 2399-2403, Mar. 1992, Medical Sciences.

Gerhäuser, C.; You, M.; Liu, J.; Moriarty, R.M.; Hawthorne, M.; Mehta, R.G.; Moon, R.C.; Pezzuto, J.M.; *Cancer Chemopreventive Potential of Sulforamate, a Novel Analogue of Sulforaphane That Induces Phase 2 Drug-metabolizing Enzymes*, Cancer Research 57, 272-278, Jan. 15, 1997.

Kolm, R.H.; Danielson, H.; Zhang, Y.; Talalay, P.; Mannervik, B.; *Isothiocyanates as substrates for human glutathione transferases: structure-activity studies*, Biochem. J., (1995), 311, 453-459 (Printed in Great Britain).

van Lieshout, E. M.M.; Bedaf, M.M.G.; Pieter, M.; Ekkel, C.; Nijhoff, W.A.; Peters, W.H.M.; *Short Communication Effects of dietary anticarcinogens on rat gastrointestinal glutathione S-transferase theta 1-1 levels*, Carcinogenesis vol. 19 No. 11 pp. 2055-2057, 1998.

Prestera, T.; Talalay, P. *Electrophile and antioxidant regulation of enzymes that detoxify carcinogens*, Proc. Natl. Acad. Sci. USA, vol. 92, pp. 8965-8969, Sep. 1995, Medical Sciences.

Fahey, J.W.; Zhang, Y.; Talalay, P.; *Broccoli sprouts: An exceptionally rich source of inducers of enzymes that protect against chemical carcinogens*, Proc. Natl. Acad. Sci. USA, vol. 94, pp. 10367-10372, Sep. 1997, Medical Sciences.

Jiao, D.; Conaway, C.C.; Wang, M.-H.; Yang, C.S.; Koehl, W.; Chung, F.-L.; *Inhibition of N-Nitrosodimethylamine Demethylase in Rat and Human Liver Microsomes by Isothiocyanates and Their Glutathione, L-Cysteine, and N-Acetyl-L-cysteine Conjugates*, Chem. Res. Toxicol. 1996, 9, 932-938.

Zhang, Y.; Kolm, R.H.; Mannervik, B.; Talalay, P.; *Reversible Conjugation of Isothiocyanates with Glutathione Catalyzed By Human Glutathione Transferases*, vol. 206, No. 2, 1995, Biochemical and Biophysical Research Communications, Jan. 17, 1995, pp. 748-755.

Faulkner, K.; Mithen, R.; Williamson, G.; *Selective increase of the potential anticarcinogen 4-methylsulphinylbutyl glucosinolate in broccoli*, Carcinogenesis vol. 19 No. 4 pp. 605-609, 1998.

Morel, F.; Langouët, S.; Mahéo, K.; Guillouzo, A.; *The use of primary hepatocyte cultures for the evaluation of chemoprotective agents*, Cell Biology and Toxicology. 1997; 13: 323-329.

Whitesell, J.K.; Wong, M.-S.; *Asymmetric Synthesis of Chiral Sulfinate Esters and Sulfoxides. Synthesis of Sulforaphane*, J. Org. Chem. 1994, 59, 597-601.

Schenk, W.A.; Dürr, M.; *Synthesis of (R)-Sulforaphane Using [CpRu((R,R)-CHIRAPHOS)]+ as Chiral Auxiliary*, Chem. Eur. J. 1997, 3, No. 5, pp. 713-716.

Ren, S.; Lien, E.J.; *Natural Products and their derivatives as cancer chemopreventive agents*, Progress in Drug Research, vol. 48 (E. Jucker, Ed.), pp. 147-171, (1997).

Begleiter, A.; Leith, M.K.; Curphey, T.J.; Doherty, G.P.; *Induction of DT-Diaphorase in Cancer Chemoprevention and Chemotherapy*, Oncology Research, vol. 9, pp. 371-382, 1997.

Dornberger, K.; Böckel, V.; Heyer, J.; Schönfeld, C.H.; Tonew, M.; Tonew, E.; *Untersuchungen über die Isothiocyanate Erysolin und Sulforaphan aus Cardaria draba L.*, Pharmazie 30, H. 12 (1975), pp. 792-796.

Loftsson, T.; Brewster, M.E.; Review Article, *Pharmaceutical Applications of Cyclodextrins. 1. Drug Solubilization and Stablization*, Journal of Pharmaceutical Sciences, Oct. 1996, vol. 85, No. 10, pp. 1017-1025.

Rajewski, R.A.; Stella, V.J.; Review Article, Pharmaceutical Applications of Cyclodextrins. 2. In Vivo Drug Delivery, Journal of Pharmaceutical Sciences, vol. 85, No. 11, Nov. 1996, pp. 1142-1169.

Irie, T.; Uekama, K.; Review Article, *Pharamaceutical Applications of Cyclodextrins. III. Toxicological Issues and Safety Evaluation*, Journal of Pharmaceutical Sciences, vol. 86, No. 2, Feb. 1997, pp. 147-162.

Stella, V.J.; Rajewski, R.A.; Review, *Cyclodextrins: Their Future in Drug Formulation and Delivery*, Pharmaceutical Research, vol. 14, No. 5, 1997, pp. 556-567.

Loftsson, T.; Brewster, M.E.; *Cyclodextrins as Pharmaceutical Excipients*, Pharmaceutical Technology Europe, May 1997, pp. 26-34.

Loftsson, T., Review, *Increasing the cyclodextri complexation of drugs and drug biovailability through addition of water-soluble polymers*, Pharmazie 53 (1998) 11, pp. 733-740.

Zhang, Y.; *Chemoprotection Against Cancer by Isothiocyannates*, A dissertation submitted to The John Hopkins University in conformity with the requirements for the degree of Doctor of Philosophy, Baltimore, Maryland; 1995.

Hoover, John E., *Remington's Pharmaceutical Sciences*; Mack Publishing Co.; Easton, PA: 1975. Part 2 Pharmaceutics: Chapter 14: Complexation; Alfonso R. Gennaro; pp. 200-210. Chapter 17: Solutions and Phase Equilibria; Theordore D. Sokoloski; pp. 229-254. Part 8: Chapter 75: Formulation; Thomas J. Macek; pp. 1355-1404. Chapter 79: Isotonic Solutions; Dwight L. Deardorff; pp. 1405-1412. Chapter 81: Stability of Pharmaceutical Products; Carl J. Lintner; pp. 1419-1428. Chapter 83: Solutions, Emulsions, and Suspension; M. Pernarowski; pp. 1436-1460. Chapter 84: Parenteral Preparations; Kenneth E. Avis; pp. 1461-1487. Chapter 85: Ophthalmic Preparations; Dwight L. Deardorff; pp. 1488-1508. Chapter 86: Extraction and Extractives; Peter W. Riebling; pp. 1509-1522. Chapter 87: Medicated Applications; Symour M. Blau; pp. 1523-1553. Chapter 88: Powders; Alvin Felmeister; pp. 1554-1575. Chapter 89: Tablets, Capsules, and Pills; Robert E. King; pp. 1576-1607. Chapter 90: Coating of Pharmaceutical Dosage Forms; Manford J. Robinson; pp. 1608-1617. Chapter 91: Prolong-Action Pharmaceuticals; Berton E. Ballard; pp. 1618-1643. Chapter 92: Aerosols; John J. Sciarra; pp. 1644-1664.

Kibbe, et al.; *Handbook of Pharmaceutical Excipients, Third Edition*; American Pharmaceutical Association, Washington, DC: 1999; pp. 165-168.

Gennaro, A.R.; *Remington: The Science and Practice of Pharmacy 21st Ed.*; Lippincott, Williams and Wilkins; 2005. Part 2: Chapter 14: Complex Formation; pp. 186-200. Chapter 16: Solutions and Phase Equilibria; Pardeep K. Gupta, Ph.D.; pp. 211-230. Chapter 17: Ionic Solutions and Electrolytic Equilibria; pp. 231-265. Chapter 18: Tonicity, Osmoticity, Osmolality, and Osmolarity; Cathy Y. Poon, PharmD.; pp. 250-265. Chapter 20: Interfacial Phenomena; Paul M. Bummer, Ph.D.; pp. 280-292. Chapter 21: Colloidal Dispersions; Bill J. Bowman, Ph.D., et al.; pp. 293-318. Chapter 22: Coarse Dispersions; James Swarbrick, DSc, Ph.D., et al.; pp. 319-337. Part 3: Chapter 24: Inorganic Parmaceutical Chemistry; Clarence A. Discher, Ph.D., et al.; pp. 361-385. Chapter 25: Organic Pharmaceutical Chemistry; Alfonso R. Gennaro, Ph.D.; pp. 386-409. Chapter 26: Natural Products; Bill J. Bowman, Ph.D., RPh., et al.; pp. 410-442. Chapter 27: Drug Nomenclature—United States Adopted Names; Pardeep K. Gupta, Ph.D., p. 443. Chapter 28: Structure-Activity Relationship and Drug Design; Randy J. Zauhar; pp. 468-478. Part 7: Chapter 65: Topical Drugs; pp. 1277-1293. Chapter 66: Gastrointestinal and Liver Drugs; John E. Hoover, BSc Pharm, RPh.; pp. 1294-1317. Chapter 92: Nutrients and Associated Substances; Joseph I. Boullata, PharmD.; pp. 1688-1718.

Goodman & Gilman's The Pharmacological Basis of Therapeutics 9th Edition; McGraw-Hill: New York, NY, 1996, *Appendix 11 Design and Optimization of Dosage Regiments; Pharmacokinetic Data,* Leslie Z. Benet, et al., pp. 1707-1711.

\* cited by examiner

STABILIZED SULFORAPHANE

CROSS-REFERENCE TO RELATED PATENT APPLICATION

This application claims priority to U.S. Provisional Patent Application Ser. No. 60/881,875, filed Jan. 23, 2007, which is incorporated by reference herein in its entirety.

BACKGROUND OF THE INVENTION

The present invention relates generally to stabilized sulforaphane, and analogs thereof. The present invention further relates generally to methods of stabilizing sulforaphane and analogs thereof.

Isothiocyanates, such as phenethyl isothiocyanate (PEITC) and sulforaphane, have been shown to inhibit carcinogenesis and tumorigensis and as such are useful chemopreventive agents against the development and proliferation of cancers. These compounds work on a variety of levels. Most notably, they have been shown to inhibit carcinogenesis through inhibition of cytochrome P450 enzymes, which oxidize compounds such as benzo[a]pyrene and other polycyclic aromatic hydrocarbons (PAHs) into more polar epoxy-diols which can then cause mutation and induce cancer development. Phenethyl isothiocyanate (PEITC) has been shown to induce apoptosis in certain cancer cell lines, and in some cases, is even able to induce apoptosis in cells that are resistant to some currently used chemotherapeutic drugs.

Sulforaphane, as discussed above, is known as an anticancer and antimicrobial compound found in cruciferous vegetables such as cabbage, broccoli, broccoli sprouts, brussel sprouts, cauliflower, cauliflower sprouts, bok choy, kale, collards, arugula, kohlrabi, mustard, turnip, red radish and watercress. In the plant, it is present in bound form as glucoraphanin, a glucosinolate. Sulforaphane is often formed from glucoraphanin on plant cell damage via an enzymatic reaction.

Various synthetic methods of producing sulforaphane are known in the art. Sulforaphane was synthesized as early as 1948 by Schimd and Karrer (Schimd H. and Karrer, P.; *Helvetica Chimica Acta*. 1948; 31; 6: 1497-1505). The Schimd synthesis results in a racemic mixture. Other methods of synthesizing sulforaphane developed since 1948 also tend to result in racemic mixtures of sulforaphane. Additionally, sulforaphane is known as an unstable oil. Due to its instability, sulforaphane is difficult to manufacture and distribute.

Cyclodextrins are a family of cyclic oligosaccharides composed of 5 or more α-D-glucopyranoside units linked 1-4. The largest well-characterized cyclodextrin contains 32 1,4-anhydroglucopyranoside units, while (as a poorly characterized mixture) 150 membered cyclic oligosaccharides (and greater) are also known.

Cyclodextrins are able to form host-guest complexes with hydrophobic molecules given the unique nature imparted by their structure. Cyclodextrins include an exterior that is sufficiently hydrophilic to impart water solubility to the cyclodextrin. The interior of the cyclodextrin is known to be hydrophilic, but can be considered hydrophobic with respect to the exterior of the cyclodextrin.

The natural cyclodextrins, in particular beta-cyclodextrin, have limited aqueous solubility and their complex formation with lipophilic drugs often results in precipitation of solid drug-cyclodextrin complexes. Thus, the solubility of beta-cyclodextrin in water is only about 18.5 mg/mL at room temperature. This low aqueous solubility is, at least partly, associated with strong intramolecular hydrogen bonding in the cyclodextrin crystal lattice. Substitution of any of the hydrogen bond-forming hydroxyl groups, even by hydrophobic moieties such as methoxy groups, will increase the aqueous solubility of beta-cyclodextrin. In addition, since these manipulations frequently produce large numbers of isomeric products, chemical modification can transform the crystalline cyclodextrins into amorphous mixtures increasing their aqueous solubility.

Cyclodextrin derivatives of current pharmaceutical interest include the hydroxypropyl derivatives of alpha-, beta- and gamma-cyclodextrin, sulfoalkylether cyclodextrins such as sulfobutylether beta-cyclodextrin, alkylated cyclodextrins such as the randomly methylated beta-cyclodextrin, and various branched cyclodextrins such as glucosyl- and maltosyl-beta-cyclodextrin (T. Loftsson and M. E. Brewster, "Cyclodextrins as pharmaceutical excipients", Pharm. Technol. Eur., 9(5), 26-34 (1997); T. Loftsson and M. E. Brewster, "Pharmaceutical applications of cyclodextrins. I. Drug solubilization and stabilization", J. Pharm. Sci. 85(10), 1017-1025 (1996); R. A. Rajewski and V. J. Stella, "Pharmaceutical applications of cyclodextrins. 2. In vivo drug delivery", J. Pharm. Sci. 85(11), 1142-1169 (1996); T. Irie and K. Uekama, "Pharmaceutical applications of cyclodextrins. 3. Toxicological issues and safety evaluation", J. Pharm. Sci., 86(2), 147-162 (1997); V. J. Stella and R. A. Rajewski, "Cyclodextrins: their future in drug formulation and delivery", Pharm. Res., 14(5), 556-567 (1997); T. Loftsson, "Increasing the cyclodextrin complexation of drugs and drug bioavailability through addition of water-soluble polymers", Pharmazie, 53, 733-740 (1998)).

In aqueous solutions, cyclodextrins form complexes with many drugs through a process in which the water molecules located in the central cavity are replaced by either the whole drug molecule, or more frequently, by some lipophilic portion of the drug structure. Once included in the cyclodextrin cavity, the drug molecules may be dissociated through complex dilution, by replacement of the included drug by some other suitable molecule (such as dietary lipids or bile salts in the GI tract) or, if the complex is located in close approximation to a lipophilic biological membrane (such as the mucosal membrane of the GI tract), the drug may be transferred to the matrix for which it has the highest affinity. Importantly, since no covalent bonds are formed or broken during the drug-cyclodextrin complex formation, the complexes are in dynamic equilibrium with free drug and cyclodextrin molecules (R. A. Rajewski and V. J. Stella, "Pharmaceutical applications of cyclodextrins. 2. In vivo drug delivery", J. Pharm. Sci. 85(11), 1142-1169 (1996)).

Various methods have been applied to the preparation of drug-cyclodextrin complexes (T. Loftsson and M. E. Brewster, "Pharmaceutical applications of cyclodextrins. I. Drug solubilization and stabilization", J. Pharm. Sci. 85(10), 1017-1025 (1996); T. Loftsson and M. E. Brewster, "Cyclodextrins as pharmaceutical excipients", Pharm. Technol. Eur., 9(5), 26-34 (1997)). In solution, the complexes are usually prepared by addition of an excess amount of the drug to an aqueous cyclodextrin solution. The suspension formed is equilibrated (for periods of up to one week at the desired temperature) and then filtered or centrifuged to form a clear drug-cyclodextrin complex solution. Since the rate determining step in complex formation is often the phase to phase transition of the drug molecule, it is sometimes possible to shorten this process by formation of supersaturated solutions through sonication followed by precipitation.

For preparation of the solid complexes, the water may be removed from the aqueous drug-cyclodextrin solutions by evaporation or sublimation, e.g. spray-drying or freeze-drying. Other methods can also be applied to prepare solid drug-cyclodextrin complexes including kneading methods, co-precipitation, neutralization and grinding techniques. In the kneading method, the drug is added to an aqueous slurry of a poorly water-soluble cyclodextrin such as beta-cyclodextrin. The mixture may be thoroughly mixed, often at elevated temperatures, to yield a paste which is then dried. This technique can frequently be modified so that it can be accomplished in a single step with the aid of commercially available mixers which can be operated at temperatures over 100° C. and under vacuum. The kneading method is a cost-effective means for preparing solid cyclodextrin complexes of poorly water-soluble drugs. Co-precipitation of a cyclodextrin complex through addition of organic solvent is also possible. Unfortunately, the organic solvents used as precipitants often interfere with complexation which makes this approach less attractive than the kneading method. It has been discovered that some organic solvents under some specific conditions, e.g. 10% (v/v) aqueous acetic acid solution, can enhance the complexation. Solid complexes of ionizable drugs can sometimes be prepared by the neutralization method wherein the drug is dissolved in an acidic (for basic drugs) or basic (for acidic drugs) aqueous cyclodextrin solution. The solubility of the drug is then lowered through appropriate pH adjustments (i.e. formation of the un-ionized drug) to force the complex out of solution. Finally, solid drug-cyclodextrin complexes can be formed by the grinding of a physical mixture of the drug and cyclodextrin and then heating the mixture in a sealed container to 60 to 90° C.

SUMMARY OF THE INVENTION

In one aspect, the invention is a method of stabilizing sulforaphane. The method includes contacting sulforaphane, or an analog thereof, and a cyclodextrin to form a complex between the sulforaphane, or analog thereof, and the cyclodextrin.

In another aspect, the invention is a composition including a complex of sulforaphane and a cyclodextrin.

In another aspect, the invention is a composition including a complex of an analog of sulforaphane and a cyclodextrin.

In yet another aspect, the invention is a pharmaceutical composition. The pharmaceutical composition includes a complex of cyclodextrin and sulforaphane, or an analog of sulforaphane, and an excipient.

In a different embodiment, the invention is a nutraceutical composition. The nutraceutical composition includes a complex of cyclodextrin and sulforaphane, or an analog of sulforaphane, and an excipient.

DETAILED DESCRIPTION OF SEVERAL EMBODIMENTS

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used on another embodiment to yield a still further embodiment. Thus, it is intended that the present invention cover such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

Figure 1:
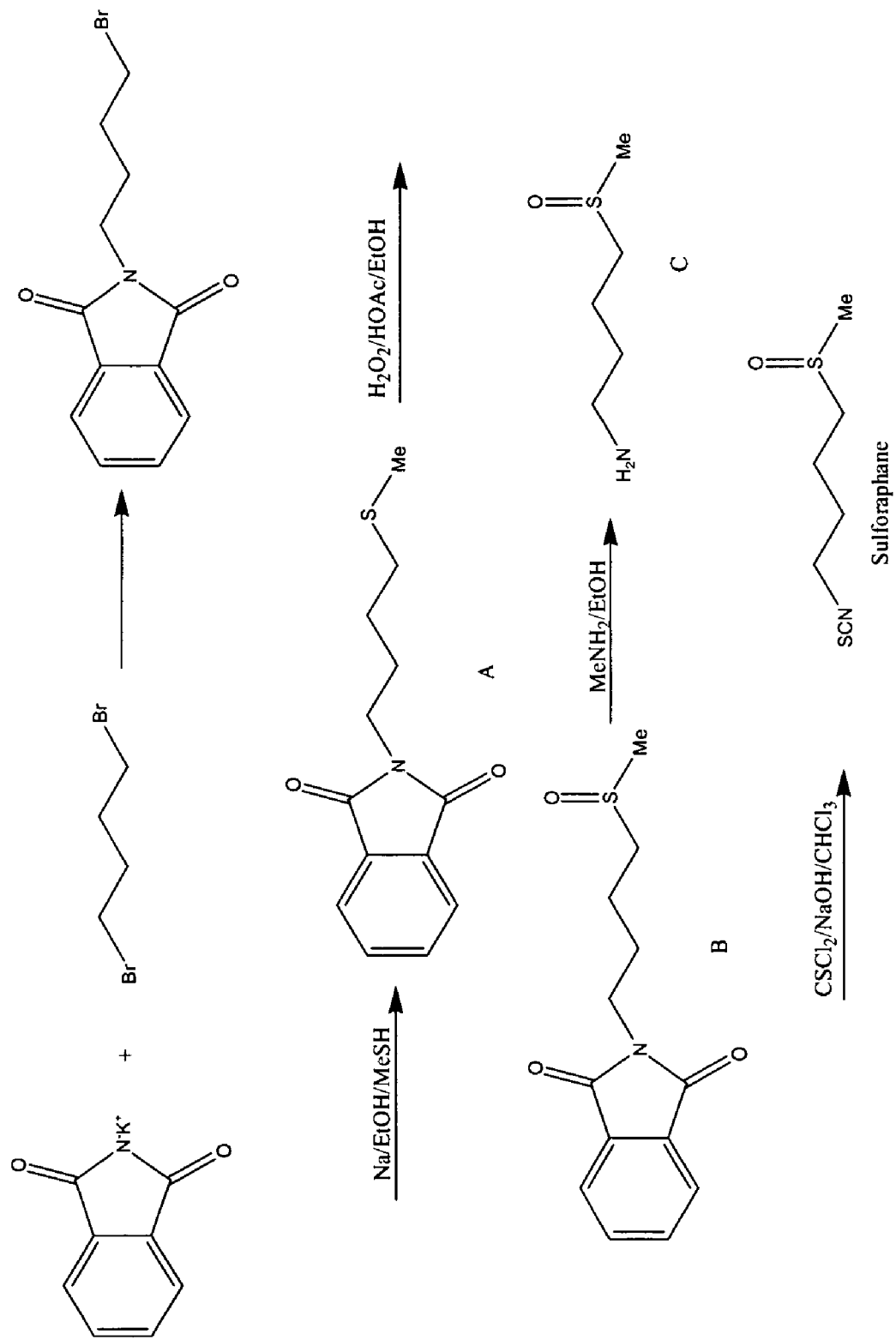
FIG. 1 is a representative reaction scheme in accordance with the present invention.

FIG. 1 represents an improved method of forming sulforaphane. In one embodiment, potassium phthalimide and tetramethylene dibromide may be combined to form bromobutylphthalimide (Intermediate A). The bromobutylphthalimide may then be combined with methyl mercaptan (MeSH) in the presence of methanol and sodium to form Intermediate B. After drying, Intermediate B may be combined with hydrogen peroxide and methyl tert-butyl ether (MTBE) to form a racemic mixture of Intermediate C.

Figure 2:
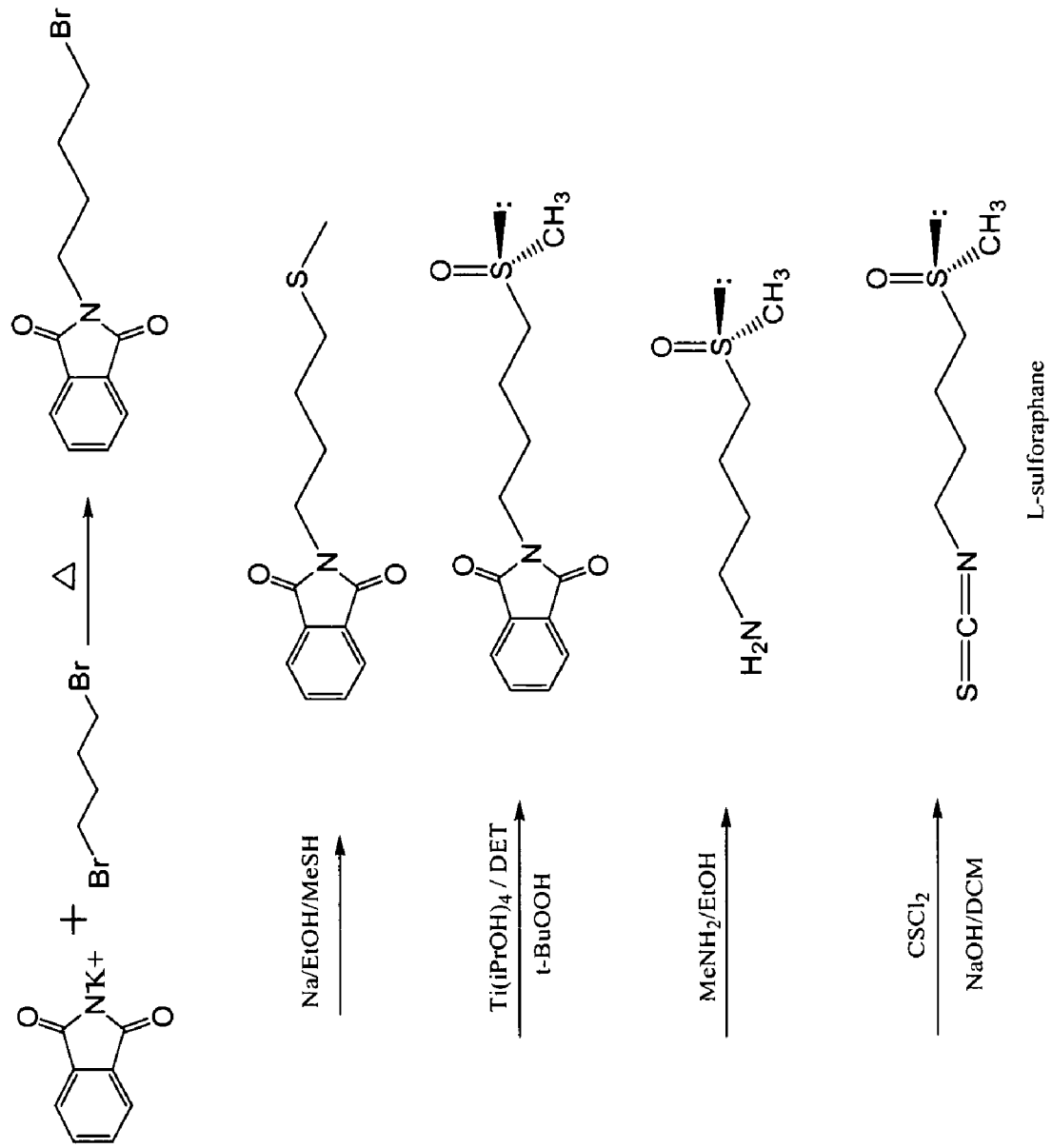
FIG. 2 is a representative reaction scheme in accordance with the present invention.

To form an enantiomerically rich Intermediate C (FIG. 2), and ultimately an enantiomerically rich sulforaphane, the asymmetric oxidation (modified Sharpless) reaction may include the addition of a Sharpless reagent, such as a 1:1:2 mixture of titanium (IV) isopropoxide, diethyl tartrate, and t-butylhydroperoxide. In another embodiment, the Sharpless reagent may be a 1:2:1:1 mixture of titanium (IV) isopropoxide, diethyl tartrate, water, and t-butylhydroperoxide at −20° C. in a solvent, such as dichloromethane. Those having ordinary skill in the art will recognize that diethyl tartrate should be used in an enantiomerically pure form to produce the enatiomerically rich sulforaphane. Accordingly, the (+) or (−) isomer should be chosen, depending on the desired chirality of sulforaphane. The oxidation is typically performed under reduced temperature (i.e., less than about 0° C.) in dichloromethane.

Intermediate C (either the racemic mixture or the enantiomerically pure version, depending on the desired sulforaphane) may then be combined with methylamine in ethanol to form Intermediate D. Finally, Intermediate D may be combined with chloroform, sodium hydroxide, and thiophosgene to form sulforaphane.

In another aspect, the invention is a composition including a complex of sulforaphane, or an analog thereof, and a cyclodextrin. In one embodiment, suitable cyclodextrins may be selected from one or more of W6 (alpha) cyclodextrin (a six sugar ring molecule), W7 (beta) cyclodextrin (a seven sugar ring molecule), W8 (gamma) cyclodextrin (an eight sugar ring molecule), and mixtures thereof. Other cyclodextrins known in the art are also contemplated as useful in the present composition and the invention shall not be limited to the specific cyclodextrins listed.

In one embodiment, the sulforaphane may be an enantiomerically rich sulforaphane. In another embodiment, the sulforaphane may be a raceimic mixture. In yet another embodiment, any ratio of enantiomers of sulforaphane may be present in the complex.

In embodiments utilizing analogs of sulforaphane, suitable analogs include, but are not limited to, 6-isothiocyanato-2-hexanone, exo-2-acetyl-6-isothiocyanatonorbornane, exo-2-isothiocyanato-6-methylsulfonylnorbornane, 6-isothiocyanato-2-hexanol, 1-isothiocyanato-4-dimethylphosphonylbutane, exo-2-(1'-hydroxyethyl)-5-isothiocyanatonorborane, exo-2-acetyl-5-isothiocyanoatonorbornane, 1-isothiocyanato-5-methylsulfonylpentane, and cis- or trans-3-(methylsulfonyl) cyclohexylmethylisothiocyanate, and mixtures thereof.

In yet another embodiment, the compositions of the present invention may include complexes of cyclodextrin with sulforaphane and analogs of sulforaphane.

In another aspect, the invention is a method of stabilizing sulforaphane and analogs thereof. The method includes contacting sulforaphane, or an analog thereof, and at least one cyclodextrin to form a complex between the sulforaphane, or analog thereof, and cyclodextrin.

The step of contacting sulforaphane, or an analog thereof, with at least one cyclodextrin may include dissolving or suspending cyclodextrin in a solvent or mixture of solvents to form a first solution or suspension. Similarly, sulforaphane, or an analog thereof, may be dissolved or suspended in the same or different solvent or mixture of solvents to form a second solution or suspension. The first solution or suspension may then be combined to form the present complex between sulforaphane, or an analog thereof, and the at least one cyclodextrin. The complex may then be separated from the solution and optionally purified, resulting in a complex of stabilized sulforaphane.

The step of contacting sulforaphane, or an analog thereof, with at least one cyclodextrin may alternatively include dissolving or suspending at least one cyclodextrin in a solvent or mixture of solvents to form a solution or suspension, and then adding sulforaphane, or an analog thereof, to the solution or suspension to form the present complex.

Additionally, the step of contacting sulforaphane, or an analog thereof, with at least one cyclodextrin may be conducted by other methods. For example, a solvent may be utilized which will fully dissolve both the sulforaphane, or analog thereof, and the cyclodextrin. In another embodiment, the cyclodextrin may be dissolved or suspended in a solvent or mixture of solvents and then placed on the rotovap. The sulforaphane, or analog thereof, may then be sprayed directly into the solution or suspension, either as a neat form or as a solution or suspension of sulforaphane, or an analog thereof, in a solvent or mixture of solvents.

The contacting step may also be accomplished by use of a biphasic solvent system. For example, the sulforaphane, or analog thereof, may be combined in separate, immiscible solvents (either as suspensions or in solution). The immiscible solvents may then be thoroughly mixed until a complex is formed. The complex may then be isolated via one of the isolation techniques discussed herein.

It may be desirable to conduct the contact step in the absence of solvents. For example, in a spray drying technique, a mist of sulforaphane, or an analog thereof, may be sprayed or misted on neat cyclodextrin to produce the present complex.

In one embodiment, the step of dissolving or suspending cyclodextrin includes dissolving or suspending a cyclodextrin selected from one or more of W6 (alpha) cyclodextrin, W7 (beta) cyclodextrin, W8 (gamma) cyclodextrin, and combinations thereof. The step of dissolving or suspending a cyclodextrin may also include dissolving or suspending one or more of other cyclodextrins known in the art.

Additionally, the step of dissolving or suspending cyclodextrin may include dissolving or suspending cyclodextrin in a solvent selected from the group including weakly non-polar to polar solvents. Suitable solvents contemplated as useful in accordance with the present invention include one or more of water, methanol, ethanol, n-propanol, iso-propanol, n-butanol, sec-butanol, iso-butanol, tert-butanol, high molecular weight alcohols, dimethyl formamide, diethyl formamide, ethylene glycol, triethyleneglyclol, glycerin, polyethyleneglycol, formic acid, acetic acid, formamide, acetone, tetrahydrofuran, dioxane, methyl ethyl ketone, high molecular weight ketones, ethyl acetate, acetonitrile, N,N-dimethylacetimide, dimethyl sulfoxide, carbon disulfide, hexane, hexane isomers, cyclohexane, heptane, heptane isomers, $C_8$-$C_{16}$ solvents, mineral oil, diethyl ether, methyl tert-butyl ether, methylene chloride, chloroform, carbon tetrachloride, benzene, nitrobenzene, toluene, and mixtures thereof.

Solvents having a dielectric constant greater than about 5.0 are contemplated as useful in accordance with the present invention for forming suspensions. Solvents having a dielectric constant greater than about 20.0 are contemplated as useful in accordance with the present invention from forming solutions. Without being bound by theory, it is believed that the most useful solvents are weakly non-polar solvents, such as ethyl acetate and dichloromethane.

Sulforaphane and sulforaphane analogs contemplated as useful for forming the present complexes include one or more of sulforaphane, 6-isothiocyanato-2-hexanone, exo-2-acetyl-6-isothiocyanatonorbornane, exo-2-isothiocyanato-6-methylsulfonylnorbornane, 6-isothiocyanato-2-hexanol, 1-isothiocyanato-4-dimethylphosphonylbutane, exo-2-(1'-hydroxyethyl)-5-isothiocyanatonorborane, exo-2-acetyl-5-isothiocyanoatonorbornane, 1-isothiocyanato-5-methylsulfonylpentane, and cis- or trans-3-(methylsulfonyl) cyclohexylmethylisothiocyanate, and mixtures thereof.

The optional step of removing the complex from solution may be conducted by processes known in the art as being useful in separation techniques. Separation techniques contemplated as useful in the present invention may include one or more of precipitation, filtration, evacuation, lyophilization (freeze drying), spray drying, and distillation. In one embodiment, the complex may be precipitated from solution by adding an alcohol, such as ethanol, to the solution.

In another embodiment, the sulforaphane may be sprayed onto cyclodextrin in a tumble drier. In this embodiment, the sprayed sulforaphane may be pure or in solution. Similarly, the cyclodextrin may be pure or may be in solution.

Each dissolving step may be conducted at temperatures suitable to the selected solvent. For example, the solubility of cyclodextrin and sulforaphane in some solvents may require elevated temperatures, whereas the solubility of cyclodextrin and sulforaphane in other solvents may require lower temperatures. In some embodiments, the solubility of cyclodextrin and sulforaphane may enable dissolving at room temperature. Those having ordinary skill in the art will recognize the relationship between cyclodextrin and sulforaphane and the selected solvents, and will be capable of making a temperature determination based on the recognized relationship.

Figure 5:
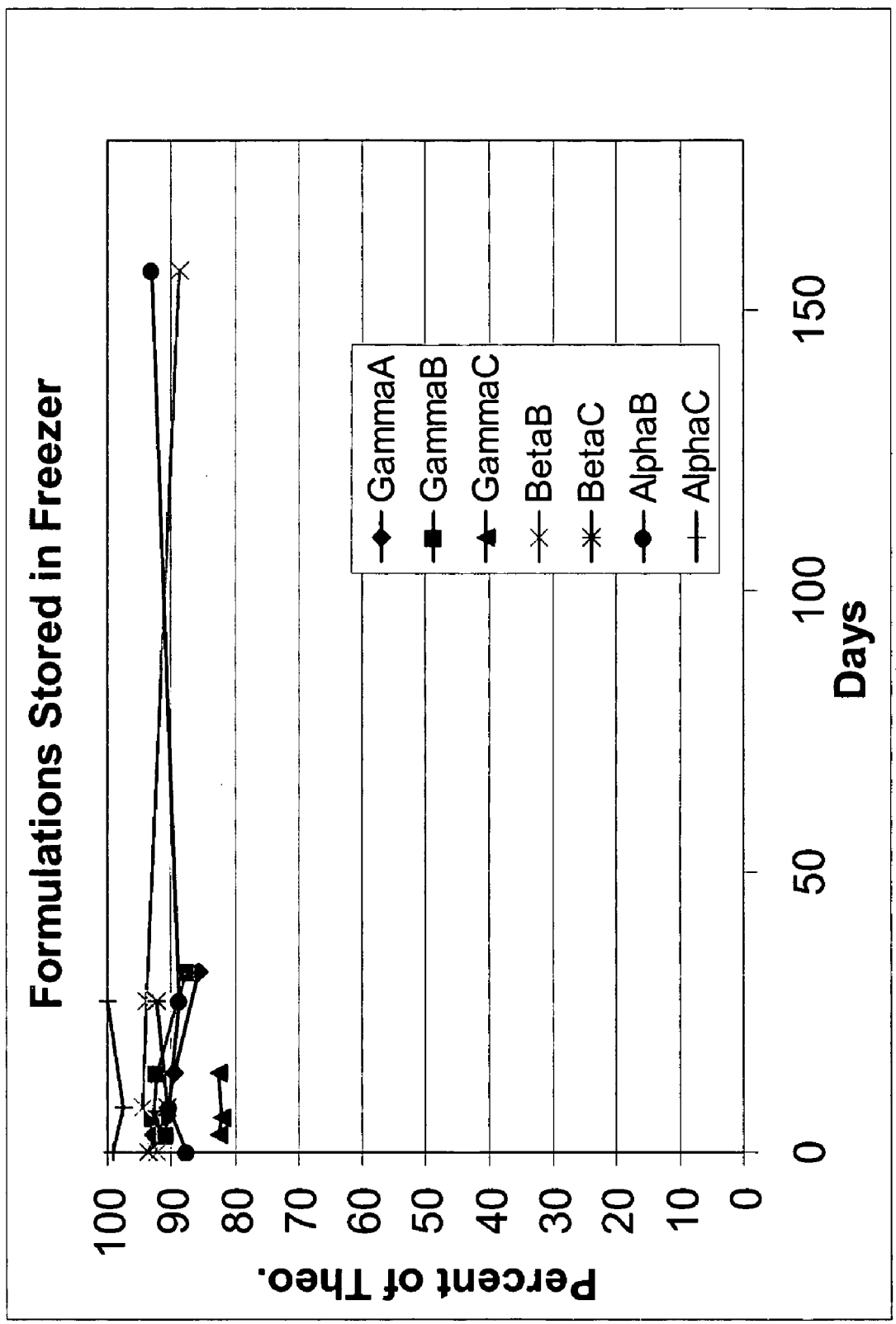
FIG. 5 is a table showing stabilization data of formulations formed in accordance with the present invention and stored in a freezer.

The stabilized sulforaphane formed in accordance with the present invention may be stored at room temperature, at elevated temperatures, or at temperatures below room temperature. The stabilized sulforaphane stored at temperatures below about room temperature demonstrated the most stability (as seen in FIG. 5), but the stabilized sulforaphane showed improved stability over non-stabilized sulforaphane at all temperatures.

Sulforaphane, like most isothiocyanates, is known in the art as being a hydrophilic molecule. Accordingly, those having ordinary skill in the art would expect a complex of sulforaphane and cyclodextrin to be more water soluble than cyclodextrin alone. Unexpectedly, the present inventors discovered that a complex of sulforaphane and cyclodextrin is actually less soluble than cyclodextrin alone. The reduced solubility further enables separation of the complex from solution, with un-complexed cyclodextrin remaining in the solution.

Without being bound by theory, it is believed that the sulforaphane, although a hydrophilic molecule, is actually hydrophobic with respect to cyclodextrin. Stated differently, sulforaphane, and its analogs, appears to be less hydrophilic than other isothiocyanates. Accordingly, when complexed into the relatively hydrophobic center of the cyclodextrins, the overall complex loses water solubility, enabling separation.

Variations on any of these manufacturing processes are known to or will be readily apparent to those skilled in the art. It is not intended that the invention be limited to any particular process of manufacture.

In another aspect, the invention is a method of providing anticancer and/or antimicrobial treatments to a subject in need of such treatment. The method includes administering stabilized sulforaphane to the subject.

For ease of reference, the present invention will be described with reference to administration to human subjects. It will be understood, however, that such descriptions are not limited to administration to humans, but will also include administration to other animals, such as mammals, unless explicitly stated otherwise. For example, besides being useful for human treatment, these combinations are also useful for treatment of mammals, including horses, dogs, cats, rats, mice, sheep, pigs, etc.

A first component of the treatment method is sulforaphane, or an analog thereof, stabilized in accordance with the methods discussed above. The components that are useful in the present invention can be of any purity or grade, as long as the preparation is of a quality and stability suitable for pharmaceutical use. The components can be provided in pure form, or they can be accompanied with impurities or commonly associated compounds that do not affect their physiological activity or safety.

The method may further include administration of other pharmaceutically acceptable components. The term "pharmaceutically acceptable" is used adjectivally herein to mean that the modified noun is appropriate for use in a pharmaceutical product.

When the present stabilized sulforaphane is supplied along with a pharmaceutically acceptable carrier, a pharmaceutical composition is formed.

A pharmaceutical composition of the present invention is directed to a composition suitable for the prevention or treatment of the disorders described herein. The pharmaceutical composition comprises stabilized sulforaphane, or an analog thereof, and at least one pharmaceutically acceptable carrier, or pharmaceutically acceptable excipient, which terms can be used interchangeably herein.

Pharmaceutically acceptable carriers and excipients are chosen such that side effects from the pharmaceutical compound(s) are minimized and the performance of the compound(s) is not canceled or inhibited to such an extent that treatment is ineffective.

The pharmaceutically acceptable carrier can also be selected on the basis of the desired route of administration of the compound(s). The desired route of administration may be one or more of oral, enteral, parenteral, injectable, buccal, and topical. For example, in a one embodiment the carrier is suitable for oral administration. In some embodiments, the composition includes a carrier or additional agent that is suitable for promoting delivery of the compound(s) to the gastrointestinal or intestinal tract.

The carrier should be acceptable in the sense of being compatible with the other ingredients of the composition and not be deleterious to the recipient. The carrier can be a solid or a liquid, or both, and is preferably formulated with the compound(s) as a unit-dose composition, for example, a tablet, which can contain from 0.01% to 95% by weight of the active compound(s).

The pharmaceutical compositions of the invention can be prepared by any of the well-known techniques of pharmacy, for example, by admixing the components.

Whether the therapeutic compounds of the present invention are administered enterally or parenterally, separately or together, each therapeutic compound may be contained in a suitable pharmaceutical formulation of any of the pharmaceutically-acceptable excipients, diluents or other formulations components described herein.

Pharmaceutically acceptable carriers include, but are not limited to, physiological saline, Ringer's, phosphate solution or buffer, buffered saline, and other carriers known in the art. Pharmaceutical compositions may also include stabilizers, anti-oxidants, colorants, and diluents. Pharmaceutically acceptable carriers and additives are chosen such that side effects from the pharmaceutical compound are minimized and the performance of the compound is not canceled or inhibited to such an extent that treatment is ineffective. The term "pharmacologically effective amount" shall mean that amount of a drug or pharmaceutical agent that will elicit the biological or medical response of a tissue, system, animal or human that is being sought by a researcher or clinician. This amount can be a therapeutically effective amount.

The present pharmaceutical compositions may be administered enterally and/or parenterally. Parenteral administration includes subcutaneous, intramuscular, intradermal, intravenous, and other administrative methods known in the art. Enteral administration includes solution, tablets, sustained release capsules, enteric coated capsules, syrups, beverages, foods, and other nutritional supplements. When administered, the present pharmaceutical composition may be at or near body temperature.

In particular, the pharmaceutical compositions of the present invention, or compositions in which they are included, can be administered orally, for example, as tablets, coated tablets, dragees, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, maize starch, or alginic acid; binding agents, for example starch, gelatin, or acacia, and lubricating agents, for example magnesium stearate, stearic acid or talc. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredients are mixed with an inert solid diluent, for example, calcium carbonate, calcium phosphate or kaolin, or as soft gelatin capsules wherein the active ingredients are present as such, or mixed with water or an oil medium, for example, peanut oil, liquid paraffin, any of a variety of herbal extracts, milk, or olive oil.

Aqueous suspensions can be produced that contain the active materials in admixture with excipients suitable for the manufacture of aqueous suspensions. Such excipients are suspending agents, for example, sodium carboxymethylcellulose, methylcellulose, hydroxypropylmethyl-cellulose, sodium alginate, polyvinylpyrrolidone gum tragacanth and gum acacia; dispersing or wetting agents may be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate.

The aqueous suspensions may also contain one or more preservatives, for example, ethyl or n-propyl p-hydroxybenzoate, one or more coloring agents, one or more flavoring agents, or one or more sweetening agents, such as sucrose or saccharin.

Oily suspensions may be formulated by suspending the active ingredients in an omega-3 fatty acid, a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Sweetening agents, such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavoring and coloring agents, may also be present.

Syrups and elixirs containing the present combination therapy may be formulated with sweetening agents, for example glycerol, sorbitol or sucrose. Such formulations may also contain a demulcent, a preservative, and flavoring and coloring agents.

The subject method and compositions in which it may be utilized can also be administered parenterally, either subcutaneously, or intravenously, or intramuscularly, or intrasternally, or by infusion techniques, in the form of sterile injectable aqueous or olagenous suspensions, or topically. Such suspensions may be formulated according to the known art using those suitable dispersing or wetting agents and suspending agents which have been mentioned above, or other acceptable agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. In addition, n-3 polyunsaturated fatty acids may find use in the preparation of injectables;

In many cases, the preferred route of administration is enteral (e.g., orally). Oral administration includes solution, tablets, sustained release capsules, enteric-coated capsules, and syrups. The pharmaceutical composition may be administered in dosage unit formulations containing conventional nontoxic pharmaceutically acceptable carriers, adjuvants, and vehicles as desired.

Compositions intended for oral use may be prepared according to any method known in the art for the manufacture of pharmaceutical compositions and such compositions may contain one or more agents selected from the group consisting of sweetening agents, flavoring agents, coloring agents and preserving agents in order to provide pharmaceutically elegant and palatable preparations.

The pharmaceutically acceptable carrier can also be selected on the basis of the desired route of administration of the compound(s). For example, in a preferred embodiment the carrier is suitable for oral administration. In some embodiments, the composition includes a carrier or additional agent that is suitable for promoting delivery of the compound(s) to the gastrointestinal or intestinal tract.

The carrier should be acceptable in the sense of being compatible with the other ingredients of the composition and not be deleterious to the recipient. The carrier can be a solid or a liquid, or both, and is preferably formulated with the compound(s) as a unit-dose composition, for example, a tablet, which can contain from 0.01% to 95% by weight of the active compound(s).

The pharmaceutical compositions of the invention can be prepared by any of the well-known techniques of pharmacy, for example, by admixing the components.

Tablets contain the active ingredient in admixture with non-toxic pharmaceutically acceptable excipients, which are suitable for the manufacture of tablets. These excipients may be, for example, inert diluents, such as calcium carbonate, sodium carbonate, lactose, calcium phosphate or sodium phosphate, granulating and disintegrating agents, for example, maize starch, or alginic acid, binding agents, for example starch, gelatin or acacia, and lubricating agents, for example magnesium stearate, stearic acid, or talc.

Pharmaceutical compositions suitable for oral administration can be presented in discrete units each containing a predetermined amount of at least one therapeutic compound useful in the present invention; as a powder or granules; as a solution or a suspension in an aqueous or non-aqueous liquid;

or as an oil-in-water or water-in-oil emulsion. As indicated, such compositions can be prepared by any suitable method of pharmacy, which includes the step of bringing into association the active compound(s) and the carrier (which can constitute one or more accessory ingredients). In general, the compositions are prepared by uniformly and intimately admixing the active compound with a liquid or finely divided solid carrier, or both, and then, if necessary, shaping the product.

For example, a tablet can be prepared by compressing or molding a powder or granules of the compound, optionally with one or more accessory ingredients. Compressed tablets can be prepared by compressing, in a suitable machine, the compound in a free-flowing form, such as a powder or granules optionally mixed with a binder, lubricant, inert diluent and/or surface active/dispersing agent(s). Molded tablets can be made by molding, in a suitable machine, the powdered compound moistened with an inert liquid diluent.

Oral delivery of the combinations of the present invention can include formulations, as are well known in the art, to provide prolonged or sustained delivery of the drug to the gastrointestinal and/or intestinal tract by any number of mechanisms. These include, but are not limited to, pH sensitive release from the dosage form based on the changing pH of the small intestine, slow erosion of a tablet or capsule, retention in the stomach based on the physical properties of the formulation, bioadhesion of the dosage form to the mucosal lining of the intestinal tract, or enzymatic release of the active drug from the dosage form. For some of the therapeutic compounds useful in the methods, combinations and compositions of the present invention the intended effect is to extend the time period over which the active drug molecule is delivered to the site of action by manipulation of the dosage form. Thus, enteric-coated and enteric-coated controlled release formulations are within the scope of the present invention. Suitable enteric coatings include cellulose acetate phthalate, polyvinylacetate phthalate, hydroxypropylmethylcellulose phthalate and anionic polymers of methacrylic acid and methacrylic acid methyl ester.

In certain embodiments, the pharmaceutical composition may comprise tablets that may be uncoated or they may be coated by known techniques to delay disintegration and absorption in the gastrointestinal tract and thereby provide a delayed action over a longer period. For example, a time delay material such as glyceryl monostearate or glyceryl distearate may be employed.

Syrups and elixirs containing the stabilized sulforaphane, or an analog thereof, may be formulated with sweetening agents, for example glycerol, sorbitol, or sucrose. Such formulations may also contain a demulcent, a preservative, and flavoring and coloring agents. Liquid dosage forms for oral administration can include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above.

Also encompassed by the present invention is buccal or "sub-lingual" administration, which includes lozenges or a chewable gum comprising the compounds, set forth herein. The compounds can be deposited in a flavored base, usually sucrose, and acacia or tragacanth, and pastilles comprising the compounds in an inert base such as gelatin and glycerin or sucrose and acacia.

The subject method of prescribing one or more of stabilized sulforaphane, stabilized analogs of sulforaphane, and compositions comprising the same can also be administered parenterally, for example, by either subcutaneously, or intravenously, or intramuscularly, or intrasternally, or by infusion techniques, in the form of sterile injectable aqueous or olagenous suspensions. Such suspensions may be formulated according to the known art using those suitable dispersing of wetting agents and suspending agents, which have been mentioned above, or other acceptable agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed, including synthetic mono- or diglycerides. In addition, n-3 polyunsaturated fatty acids may find use in the preparation of injectables.

Pharmaceutical compositions suitable for parenteral administration can conveniently comprise sterile aqueous preparations of a compound of the present invention. These preparations are preferably administered intravenously, although administration can also be effected by means of subcutaneous, intramuscular, or intradermal injection or by infusion. Such preparations can conveniently be prepared by admixing the compound with water and rendering the resulting solution sterile and isotonic with the blood. Injectable compositions according to the invention will generally contain from 0.01 to 10% w/w of a compound disclosed herein.

Injectable preparations, for example, sterile injectable aqueous or oleaginous suspensions may be formulated according to the known art using suitable dispersing or setting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The active ingredients may also be administered by injection as a composition wherein, for example, saline, dextrose, or water may be used as a suitable carrier. A suitable daily dose of each active therapeutic compound is one that achieves the same blood serum level as produced by oral administration as described above.

Pharmaceutical compositions suitable for topical application to the skin preferably take the form of an ointments, creams, lotions, pastes, gels, sprays, powders, jellies, collyriums, solutions or suspensions, aerosols, or oils. Carriers, which can be used, include petroleum jelly (e.g., Vaseline®), lanolin, polyethylene glycols, alcohols, and combinations of two or more thereof. The active compound or compounds are generally present at a concentration of from 0.01 to 50% w/w of the composition, for example, from 0.01 to 2%.

The present invention may also include safe and effective amounts of isotonicity agents, e.g., salts, such as sodium chloride, and more preferably non-electrolyte isotonicity agents such as sorbitol, and mannitol.

The solubility of the components of the present compositions may be enhanced by a surfactant or other appropriate co-solvent in the composition. Such co-solvents include polysorbate 20, 60, and 80, polyoxyethylene/polyoxypropylene surfactants (e.g., Pluronic F-68, F-84 and P-103), cyclodextrin, or other agents known to those skilled in the art. Typically, such co-solvents are employed at a level of from 0.01% to 2% by weight.

Pharmaceutically acceptable excipients and carriers encompass all the foregoing and the like. The above considerations concerning effective formulations and administration procedures are well known in the art and are described in standard textbooks. See e.g. Gennaro, A. R., *Remington: The Science and Practice of Pharmacy*, 20$^{th}$ Edition, (Lippincott, Williams and Wilkins), 2000; Hoover, John E., *Remington's Pharmaceutical Sciences*, Mack Publishing Co., Easton, Pa., 1975; Liberman, et al., Eds., *Pharmaceutical Dosage Forms*, Marcel Decker, New York, N.Y., 1980; and Kibbe, et al., Eds., *Handbook of Pharmaceutical Excipients* (3$^{rd}$ Ed.), American Pharmaceutical Association, Washington, 1999.

In the present method, a subject in need of treatment and/or prevention of the disorders described herein and/or related conditions may be treated with an amount of the present stabilized sulforaphane and/or stabilized analogs of sulforaphane, where the amount of the individual components provides a dosage or amount that is sufficient to constitute a treatment or prevention effective amount.

As used herein, an "effective amount" means the dose or amount of the present combination therapy to be administered to a subject and the frequency of administration to the subject which is readily determined by one of ordinary skill in the art, by the use of known techniques and by observing results obtained under analogous circumstances and has some therapeutic action. The dose or effective amount to be administered to a subject and the frequency of administration to the subject can be readily determined by one of ordinary skill in the art by the use of known techniques and by observing results obtained under analogous circumstances.

The phrase "therapeutically-effective" and "effective for the treatment, prevention, or inhibition," are intended to qualify the amount of each agent for use in the therapy which will achieve the goal of providing an anti-cancer, chemopreventive, antibactieral, and/or other medicinal therapy.

The amount of the present stabilized compounds that is required to achieve the desired biological effect will, of course, depend on a number of factors such as the specific compound chosen, the use for which it is intended, the mode of administration, and the host to be treated and the clinical condition of the recipient.

A carcinogenic, tumorigenic, or anti-bacterial symptom is considered ameliorated or improved if any benefit is achieved, no matter how slight.

A "therapeutically effective amount" is intended to qualify the amount of stabilized sulforaphane required to treat, prevent or inhibit carcinogenises, tumorigenesis, and bacteria-induced conditions, such as ulcers.

As used herein, the terms "prophylactically effective" refer to an amount of stabilized sulforaphane that causes a decrease in the frequency of incidence of cancers or bacteria-induced conditions, such as ulcers. The term "prophylactic" refers to the prevention of cancers and bacteria-induced conditions, whereas the term "therapeutic" refers to the effective treatment of an existing cancer or bacteria-induced condition.

As used herein, an "effective amount" means the dose or amount to be administered to a subject and the frequency of administration to the subject, which is readily determined by one having ordinary skill in the art, by the use of known techniques and by observing results obtained under analogous circumstances.

Dosages for the present compositions and methods provided herein may be determined and adjusted based on the efficacy demonstrated in providing a chemoprotective or chemopreventative result. In addition, one of ordinary skill in the art will know how to measure and quantify the presence or absence of carcinogenesis or tumorigenesis symptoms.

Preferred dosages for the present compositions are those that are effective to provide a chemoprotective, chemopreventative, and/or anti-bacterial effect.

Those skilled in the art will appreciate that dosages may also be determined with guidance from Goodman & Gilman's *The Pharmacological Basis of Therapeutics*, Ninth Edition (1996), Appendix II, pp. 1707-1711.

The following examples describe various embodiments of the present invention. Other embodiments within the scope of the claims herein will be apparent to one skilled in the art from consideration of the specification or practice of the invention as disclosed herein. It is intended that the specification, together with the examples, be considered to be exemplary only, with the scope and spirit of the invention being indicated by the claims which follow the examples. In the examples, all percentages are given on a weight basis unless otherwise indicated.

EXAMPLES

Example 1

This example illustrates a method of forming a racemic mixture of sulforaphane. The reaction pathway is illustrated as FIG. 1.

Intermediate A:

Potassium phthalimide (65 g, 350 mmol, 1.00 eq.) and tetramethylene dibromide (200 g, 930 mmol, 2.66 eq.) were combined (neat) and heated for 12 hours. The excess tetramethylene dibromide was removed via rotary-evaporation (rotovap). The resulting residue was digested with ethanol and filtered. The material that crystallized on standing was filtered, washed with ethanol, and dried in vacuo. A second crop was obtained by concentration of combined filtrate and washings. The combined mass of crops was 60.5 g (61% yield).

Intermediate B:

All glassware was dried ($N_2$ stream/heat gun). A 2 L round bottom flask, equipped with a stir bar, was charged with 300 mL anhydrous methanol. Sodium (6.48 g, 281.8 mmol, 1.06 eq.) was added carefully. At room temperature, methyl mercaptan (MeSH, 13.56 g, 281.8 mmol, 1.06 eq) was charged via syringe in one portion. [MeSH (gaseous) was trapped in a separate multi-neck round bottom flask in a dry-ice/acetone bath equipped with a dry-ice/acetone cold finger trap and transferred in a dry/freezer cooled syringe.] Bromobutylphthalimide (75.0 g, 265.8 mmol, 1.00 eq.) was suspended in 300 mL anhydrous methanol and charged to the reaction. The reaction was allowed to stir at room temperature overnight under nitrogen. A reaction aliquot analyzed by gas chromatography confirmed the reaction went to completion. Next, 300 mL of water was added to the reaction and the alcohol was removed via rotovap distillation at which point product precipitated out of solution. The product (white solid) was filtered off and washed with 2×150 ml cold water. The product was dried in a vacuum oven at 40° C. overnight to give 65.2 g (98% yield) white solid which was 98.4% pure via gas chromatography. The product was stored under nitrogen.

This procedure was adapted from a reported procedure in *Helvetica Chimica Acta*. 1948: 31; 6: 1497-1505. The current procedure differed from the reported procedure in several aspects. First, the report procedure utilized a reaction solvent that was absolute alcohol (EtOH). Also, after allowing the reaction to stir overnight at room temperature, the reported procedure included the additional step of refluxing the mixture for several hours. The original reference also worked up the reaction differently. For example, the NaBr was filtered out of the alcohol and the filtrate was concentrated to residue. The residue was next dissolved in a carbon disulfide-ether mixture and washed with water and sodium bicarbonate solution. The paper yield over three experiments was between about 82 and 92%.

Those having ordinary skill in the art will recognize that the present procedure includes fewer steps, reducing the overall reaction time, and results in higher yields than those of the previously reported procedure.

Intermediate C:

Intermediate B (45.0 g, 180.5 mmol, 1.00 eq.) was suspended (not fully dissolved) in 580 mL of a 1:1 mixture of acetic acid and ethanol. The suspension was cooled over an ice/brine bath. Hydrogen peroxide solution (120.014 M AQ, previously titrated, 15.02 mL, 180.5 mmol, 1.00 eq.) was added and the reaction allowed to stir, warming to room temperature overnight. The material dissolved during the process to give a light yellow solution. An aliquot was checked by thin layer chromatography (neat EtOAc) to confirm reaction completion. The reaction was concentrated via rotovap (not completely, ~90% of the solvent removed) and diluted with 400 mL of methyl tert-butyl ether (MTBE) at which point product (light yellow solid) precipitated out of solution. The solid was filtered off and washed with an additional 100 mL MTBE. A second crop from the MTBE filtrate was collected. Combined mass of both crops (after further drying) was 44.5 g (95% yield) with HPLC purity of ~95%. NMR showed residual acetic acid. The material was not further purified.

This procedure was adapted from the above referenced reported procedure. The reported procedure provided two different processes. The first used anhydrous acetone as the solvent, no acid, and the reaction was held at room temperature for five days. The second process called for glacial acetic acid and cooling of the reaction to moderate the exotherm. The reference work-up is precipitation of the product using absolute ether.

Those having ordinary skill in the art will recognize the present procedure results in reduced reaction times and can be conducted at ambient reaction conditions.

Intermediate D:

A dried (N$_2$ stream/heat gun) 500 mL round bottom flask, equipped with a stir bar, was charged with Intermediate C (35.34 g, 133.19 mmol, 1.0 eq.). Methylamine (33 wt % solution in ethanol, 175 mL, ~10 eq.) was charged into the round bottom flask. The solid Intermediate C slowly went into solution over approximately 45 minutes. After an additional hour, solid began precipitating out of solution (presumably methyl phthalimide). The reaction was allowed to stir, well-sealed, at room temperature overnight. The reaction was diluted with 50 mL ethanol (some of the solid dissolved) and filtered to remove the methyl phthalimide by-product. The solid by-product was washed with an additional 2×25 mL ethanol. The filtrate was concentrated via rotovap (bath temperature less than about 30° C.). The residue was adsorbed onto 50 g of silica and columned over 50 g of silica. Three column volumes of dichloromethane were enough to wash off residual methylphthalimide by-product. The product was eluted using 40% of 9:1 methanol:ammonium hydroxide in dichloromethane. 19.1 g of a light yellow oil that was pure via GC but contained water and ammonium hydroxide by NMR was collected. The oil was kuglrhor distilled at 1 mbar and 185° C. air bath temperature to give 11.80 g of a yellow oil (65.5% yield) that was greater than 99% pure via GC. The pot residue weighted 3.14 g signaling possible thermal degradation.

Sulforaphane:

A one liter round bottom flask equipped with a stir bar was charged with Intermediate D (10.8 g, 79.9 mmol, 1.00 eq.), 300 mL of chloroform, and 133 mL of 1N NaOH (aq) solution (132.8 mmol, 1.66 eq.). To the biphasic solution, thiophosgene (13.78 g, 119.8 mmol, 1.50 eq.) was charged. The reaction was stirred vigorously for one hour before an aliquot was checked by thin layer chromatography. The mixture was diluted with ~300 mL chloroform and 200 mL brine. The organics were removed and aqueous re-extracted with 2×500 mL chloroform. The organics were combined, dried over sodium sulfate, and concentrated. The residue was adsorbed onto 20 g silica and columned over 50 g silica, eluting with 0 to 4% methanol in chloroform. 12.14 grams (85.7% yield) of the desired product was collected as a light yellow oil.

Stabilization of Sulforaphane:

Sulforaphane was formulated with three types of cyclodextrins: W6 (alpha), W7 (beta), and W8 (gamma). These cyclodextrins were purchased from Wacker Chemie AG (CAVAMAX™ brand, either food grade or pharmaceutical grade).

The sulforaphane was formulated using three different conditions/procedures:

Type A: Dissolve all (cyclodextrin/sulforaphane) in nitrogen sparged water (remove CO$_2$). Let stir overnight at room temperature. Dry down to constant weight under vacuum (maintain bath at less than 30° C.). (Recovery is theoretically quantitative. There is loss of mass due to drying of cyclodextrin, which is generally 5 to 10% water wet.) Typical loads were ~1% wt/wt sulforaphane to cyclodextrin. The theoretical load is calculated from the amount of sulforaphane going in to the formulations divided by the final dry down mass.

Type B: to a suspension of cyclodextrin in ethyl acetate, add sulforaphane. Let stir overnight at room temperature. Dry down to constant weight under vacuum (maintain bath at less than 30° C.). (Recovery is theoretically quantitative. There is loss of mass due to drying of cyclodextrin which is generally 5 to 10% water wet.) Typical loads were ~1 to 5% wt/wt sulforaphane to cyclodextrin. The theoretical load is calculated from the amount of sulforaphane going in to the formulation divided by the final dry down mass.

Type C: To a saturated solution of cyclodextrin in water, add sulforaphane. Let the solution sit overnight. Collect the precipitate via filtration. If no precipitate forms, cool at –4° C. overnight. Dry down to a constant weight under vacuum (maintain bath at less than 30° C.). Recovery is generally poor: 28% with Alpha cyclodextrin, 26% using beta cyclodextrin, and 62% for gamma cyclodextrin. The theoretical load is calculated using NMR analysis of the dried down formulation and is typically between 7 and 13% depending on the cyclodextrin used.

Table 1 includes a listing of each of the formulations prepared according to the procedures of Type A, Type B, and Type C described above.

TABLE 1

Formulations produced

| Sample Key | Cyclodextrin | Formulation type | Theoretical Load |
|---|---|---|---|
| alphaB | alpha CD | B | 4.73% |
| alphaC | alpha CD | C | 7.1% |
| betaB | beta CD | B | 5.15% |
| betaC | beta CD | C | 13.3% |
| gammaA | gamma CD | A | 1.01% |
| gammaB | gamma CD | B | 0.94% |
| gammaC | gamma cd | C | 9.8% |

Stability Analysis Summary

Analysis Overview: The sulforaphane formulations were analyzed via HPLC (UV detection at 254 nm) using an internal standard (DEET) method. An assumption is made that the sulforaphane completely disassociates from the cyclodextrin under the chromatographic conditions. A sulforaphane standard (stored in a freezer) is used to determine the response factor for each analysis. Initial work demonstrated linearity of response versus concentration of this standard. The response factor (RF) of all the standard injections throughout all analyses has remained stable demonstrating the stability of the standard in the freezer.

Storage Conditions: The samples were stored under three conditions: Capped and at room temperature, capped and stored in the freezer (−30° C.), and open and stored in a 40° C. oven. These samples were analyzed for sulforaphane load over time. The stabilization of the different samples and different storage conditions may be seen in FIGS. 3-5.

Sample Preparation Example: A 20 mg to 50 mg (carefully weighed) formulation sample is dissolved in 1 mL of internal standard solution (DEET in DMF). The amount of ISTD solution is also carefully weighed. The sample is further diluted with 1 mL of nitrogen sparged deionized water. The samples are sonicated for approximately ten minutes and filtered through ha 0.45 μm nylon filter. The samples are then analyzed by HPLC UV detection at 254 nm.

Chromatographic Conditions

| | |
|---|---|
| Column: | Agilent Eclipse XDB-C18, 5 μm, 250 × 4.6 mm at 30° C. |
| Solvent A: | 0.1% formic acid in water |
| Solvent B: | MeCN |
| Gradient: | 5% to 100% Solvent B in Solvent A over 30 minutes |
| Flow: | 1.5 mL/minute |
| Detector: | UV 254 nm, ESI-MS (pos/neg) for confirmation |
| Retention: | Sulforaphane: 9.2 min. DEET: 15.5 min. |

Analysis Results: The results are presented as percent of theoretical load versus time (The calculation for theoretical was described above.)

Figure 3:
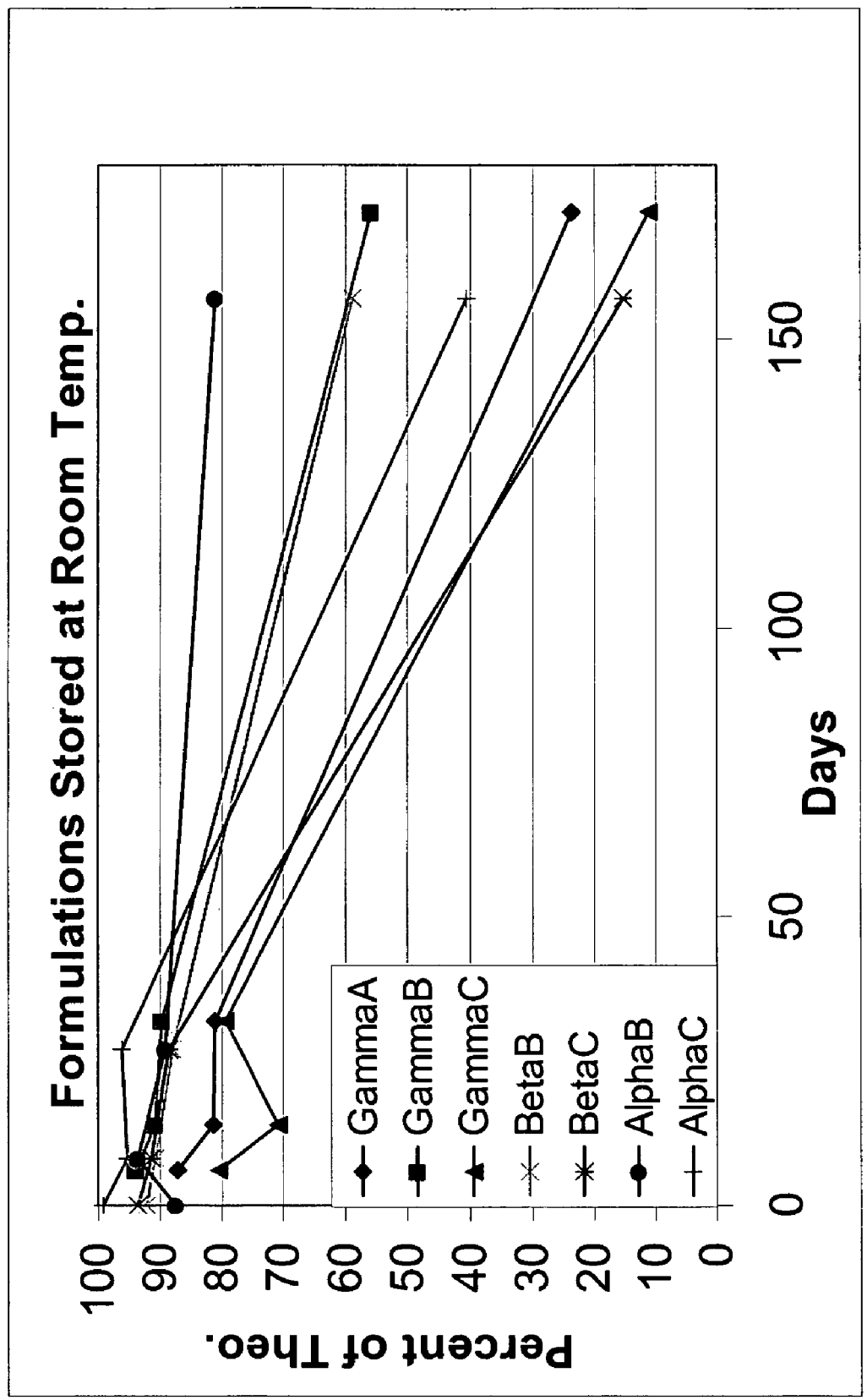
FIG. 3 is a table showing stabilization data of formulations formed in accordance with the present invention and stored at room temperature.

FIG. 3 demonstrates the stabilization data of the formulations stored at room temperature for 150 days. As can be seen in FIG. 3, the alphaB sample maintained the highest percentage of theoretical load after 150 days at room temperature. The gammaC sample lost the greatest percentage of theoretical load over the same time period.

Figure 4:
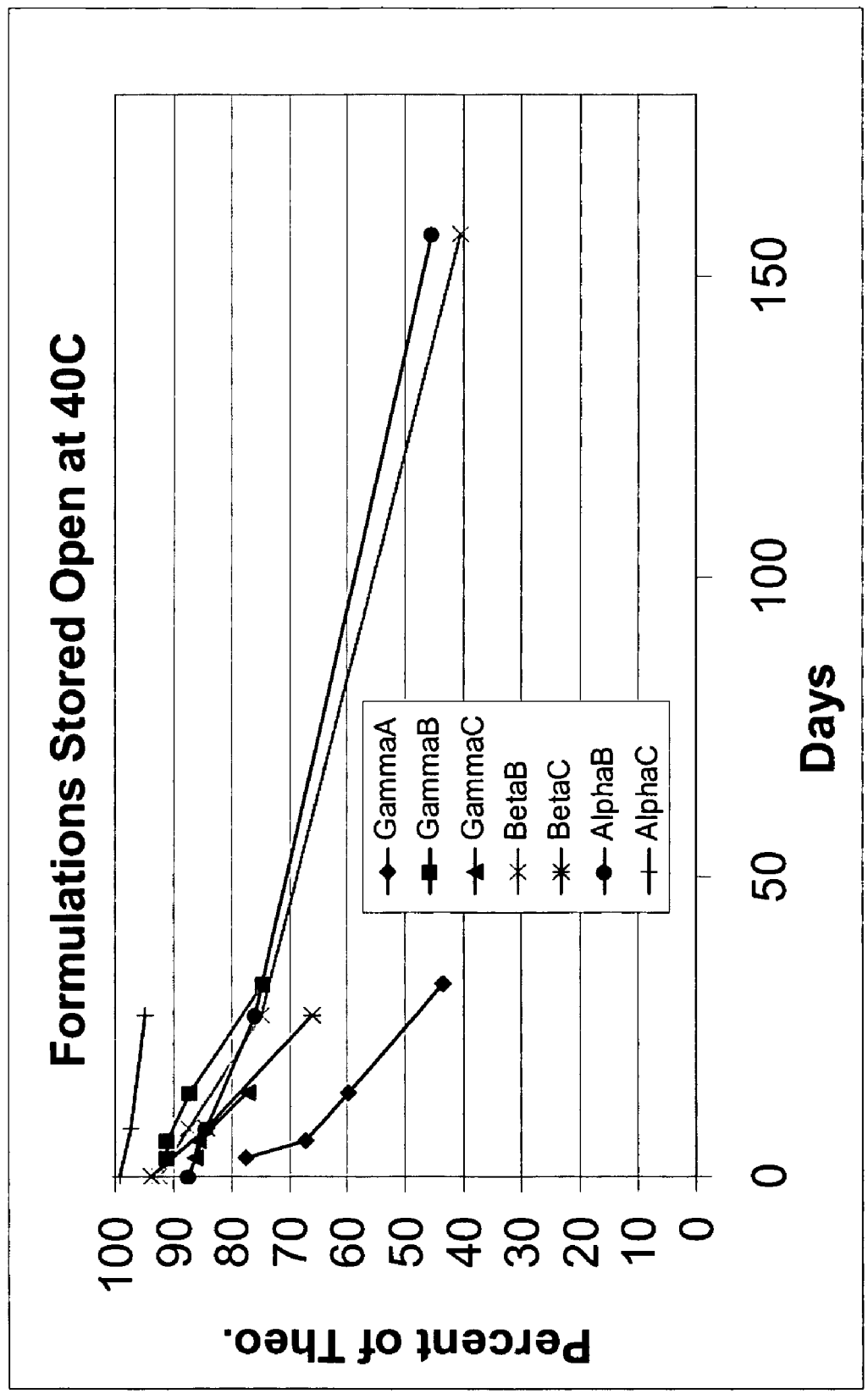
FIG. 4 is a table showing stabilization data of formulations formed in accordance with the present invention and stored in open containers at 40° C.

FIG. 4 demonstrates the stabilization data of the formulations stored in an open container in a 40° C. oven for up to about 150 days. Several samples were removed earlier than 150 days. The alphaC sample showed the slowest rate of degradation over approximately the first 40 days. After 150 days, the betaB sample maintained 40% of the original theoretical load of sulforaphane and the alphaB sample maintained about 45% of the original theoretical load.

FIG. 5 demonstrates the stabilization data of the formulations stored in a freezer. The alphaB and the betaB samples remained in the freezer for approximately 150 days. The other samples remained in the freezer for approximately 40 days. After 40 days, each sample still maintained greater than 80% of their original theoretical loads. After 150 days, each of alphaB and betaB maintained approximately 90% of their original theoretical loads.

Example 2

This example demonstrates extended stability studies for the present stabilized sulforaphane compositions.

Sulforaphane was re-synthesized using the previously described process on an increased scale. The synthesis resulted in about 94 gram of product. Three formulations were reproduced, the alphaB, alphaC, and betaB, as shown in Table 2:

TABLE 2

Sample Descriptions

| Sample | Cycoldextrin | Method of Formulation | Result |
|---|---|---|---|
| AlphaB (Sample ID: 122PAL31) | W6 (Alpha) | Type B: 20.15 grams of Sulforaphane were added to a suspension of 380.0 grams of alpha CD in 9.1 liters of EtOAc. The mixture was stirred overnight at room temperature. The mixture was dried to constant weight under vacuum (at a bath temperature <30° C.). | Final dried mass 370 grams. Percent Recovery: Quant. Theoretical Load = 5.44%. Experimental Load (T-Zero Analysis) = 4.91% |
| AlphaC (Sample ID: 122PAL33) | W6 (Alpha) | Type C: 25.10 grams of Sulforaphane was added to a stirring saturated solution of CD in H$_2$O. The mixture was allowed to stir for three hours at room temperature and was then placed in a refrigerator overnight. The precipitate was collected via filtration and further dried to constant weight under vacuum (maintain bath at <30° C.). | Final dried mass 89.7 grams. Percent Recovery: 23% Theoretical Load = N/A. Experimental Load (T-Zero Analysis) = 6.42% |

TABLE 2-continued

Sample Descriptions

| Sample | Cycoldextrin | Method of Formulation | Result |
| --- | --- | --- | --- |
| BetaB (Sample ID: 122PAL35) | W7 (Beta) | Type B: 17.50 grams of Sulforaphane was added to a suspension of 332.5 grams of beta CD in 8.9 liters of EtOAc. The mixture was stirred overnight at room temperature. The mixture was dried to constant weight under vacuum (at a bath temperature <30° C.). | Final dried mass 334 grams. Percent Recovery: Quant. Theoretical Load = 5.24%. Experimental Load (T-Zero Analysis) = 5.19% |

The sulforaphane formulations were analyzed via HPLC (UV detection at 254 nm) using an internal standard (DEET) method. A sulforaphane standard (stored in a freezer) was used to determine the response factor for each analysis. Initial work demonstrated linearity of response versus concentration of this standard. The response factor (RF) of all the standard injections throughout all analyses has remained stable demonstrating the stability of the standard in the freezer.

Sample Preparation:

A ca. 300 mg (carefully weighed) formulation sample was dissolved in 8 mL of internal standard solution (DEET in DMF, ca 2 mg/mL). The amount of ISTD solution was also carefully weighed. The sample was further diluted with 8 mL of nitrogen sparged DI water. The samples were sonicated for ~10 minutes and filtered through a 0.45 μm nylon filter. The samples were then analyzed by HPLC UV detection at 254 nm.

Figure 6:
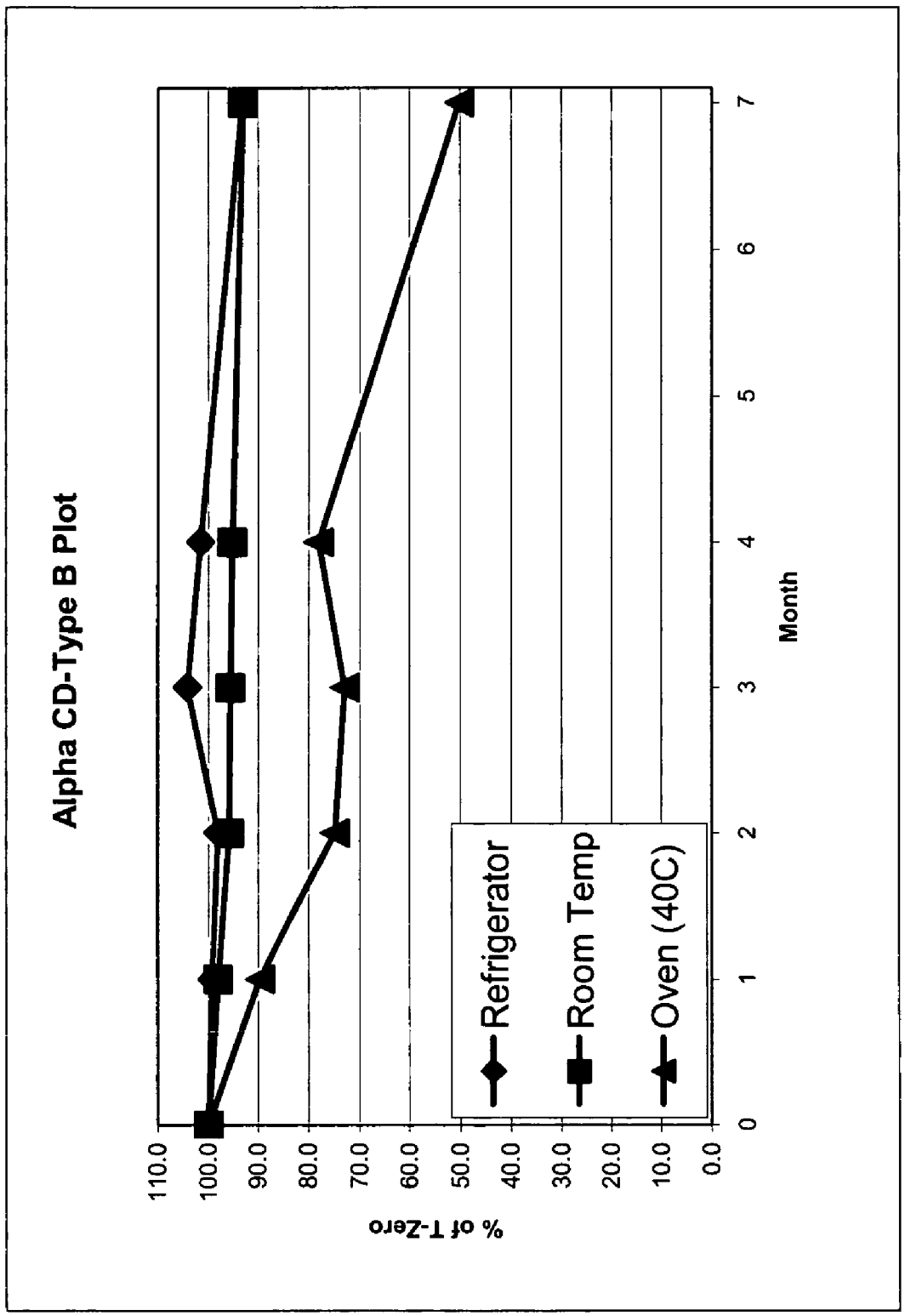
FIG. 6 is a table showing long-term stabilization data of alphaB compositions in accordance with the present invention.

Chromatographic Conditions:
Column: Agilent Eclipse XDB-C18, 5 μm, 250×4.6 mm, 250×4.6 mm @ 30° C.
Solvent A: 0.1% Formic acid in $H_2O$
Solvent B: MeCN
Gradient: 5% to 100% Solvent B in Solvent A over 30 minutes
Flow: 1.5 mL/minute
Detector: UV 254 nm, ESI-MS (pos/neg) for confirmation
Retention Times: Sulforaphane: 9.2 minutes DEET: 15.5 minutes Analysis Results: The results are presented as percent of the "time zero" load versus time. The results of the stabilization study of the alphaB sample are shown in FIG. 6. As can be seen, the alphaB sample (described in Table 2 above) maintained its integrity for 7 months at room temperature and at reduced temperatures, while degrading approximately 50% in an elevated temperature environment (40° C.).

Figure 7:
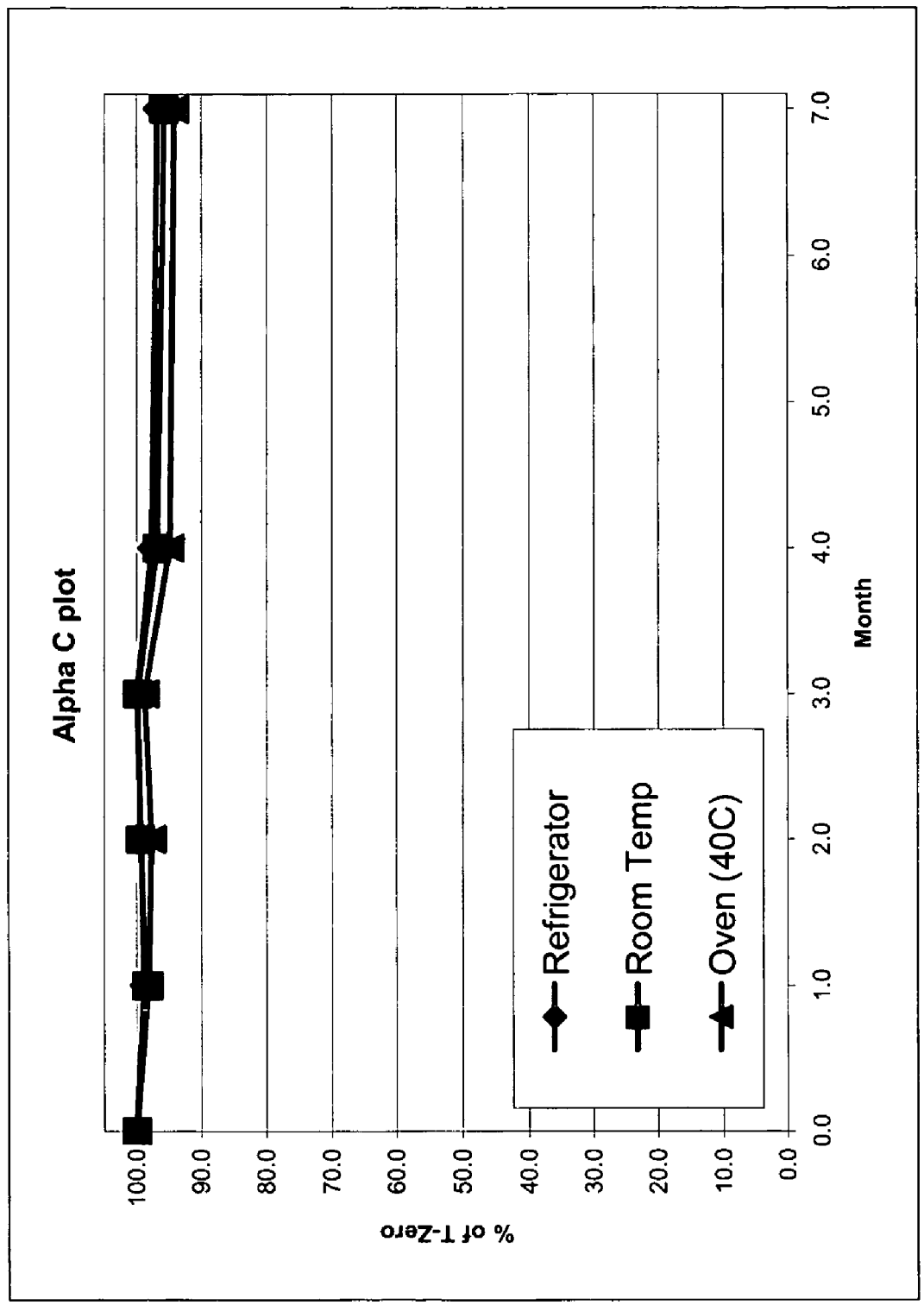
FIG. 7 is a table showing long-term stabilization data of alphaC compositions in accordance with the present invention.

FIG. 7 demonstrates the stability data generated by the alphaC sample (described in Table 2 above). As can be seen the stability of the alphaC complex was maintained over a period of seven months at reduced temperatures, at ambient temperatures, and at elevated temperatures.

Figure 8:
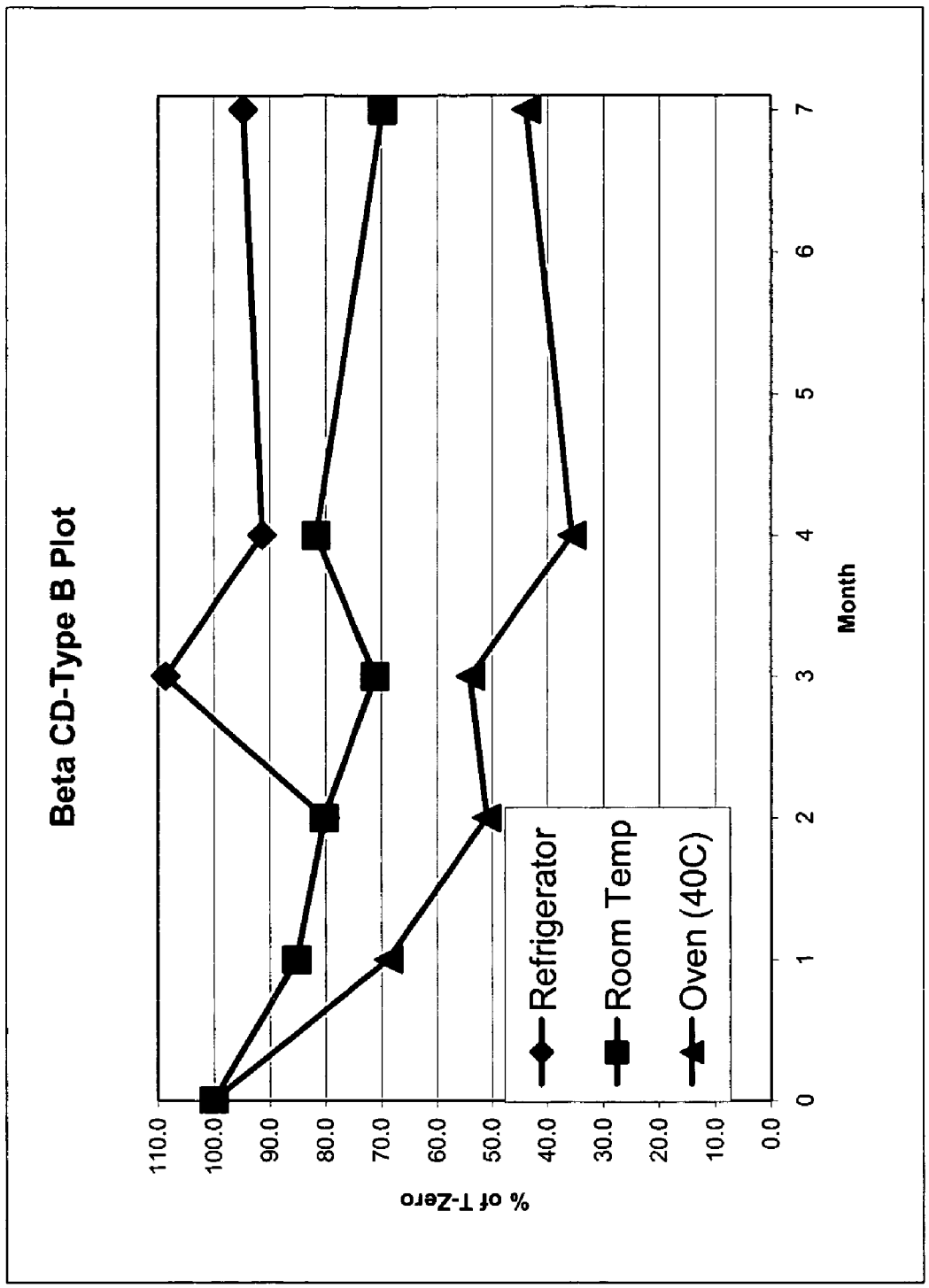
FIG. 8 is a table showing long-term stabilization data of betaB compositions in accordance with the present invention.

FIG. 8 demonstrates the stability data generated by the betaB sample (described in Table 2 above). As can be seen, the stability of the betaB complex decreased slightly over a period of four months at reduced temperatures and at ambient temperatures, before stabilizing for the remaining three months of the study. The elevated temperature sample of the betaB complex showed more degradation, but still demonstrated improved stability beyond what would be expected for a non-stabilized sulforaphane sample.

These examples demonstrate the present sulforaphane complexes provide improved stability for sulforaphane. Accordingly, the sulforaphane may be more easily manufactured and distributed as an agent for anticancer treatments, antimicrobial treatments, and other uses. Moreover, this stability data demonstrates that sulforaphane compositions may be stored for longer periods of time before treatment.

All references cited in this specification, including without limitation, all papers, publications, patents, patent applications, presentations, texts, reports, manuscripts, brochures, books, internet postings, journal articles, periodicals, and the like, are hereby incorporated by reference into this specification in their entireties.

The discussion of the references herein is intended merely to summarize the assertions made by their authors and no admission is made that any reference constitutes prior art. Applicants reserve the right to challenge the accuracy and pertinency of the cited references.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged both in whole or in part.

What is claimed is:

1. A method of stabilizing sulforaphane, or an analog thereof, the method comprising:
    contacting sulforaphane or an analog of sulforaphane selected from one or more of 6 isothiocyanato-2-hexanone, exo-2-acetyl-6-isothiocyanatonorbornane, exo-2-isothiocyanato-6-methylsulfonylnorbornane, 6-isothiocyanato-2-hexanol, 1-isothiocyanato-4-dimethylphosphonylbutane, exo-2-(1'-hydroxyethyl)-5-isothiocyanatonorborane, exo-2-acetyl-5-isothiocyanoatonorbornane, 1-isothiocyanato-5-methylsulfonylpentane, and cis- or trans-3-(methylsulfonyl)-cyclohexylmethyl-isothiocyanate, and mixtures thereof, and at least one cyclodextrin to form a complex between the sulforaphane, or analog of sulforaphane, and the at least one cyclodextrin.

2. A method according to claim 1, wherein the at least one cyclodextrin is selected from the group consisting of W6 (alpha) cyclodextrin, W7 (beta) cyclodextrin, W8 (gamma) cyclodextrin, and mixtures thereof.

3. A method according to claim 1, wherein the step of contacting sulforaphane, or an analog thereof, and at least one cyclodextrin comprises:
    dissolving or suspending the at least one cyclodextrin in a solvent or mixture of solvents to form a solution or suspension; and dissolving or suspending the sulforaphane, or an analog thereof, in the solution or suspension.

4. A method according to claim 3, wherein the solvent is selected from the group consisting of water, methanol, ethanol, n-propanol, iso-propanol, n-butanol, sec-butanol, iso-butanol, tert-butanol, high molecular weight alcohols, dimethyl formamide, diethyl formamide, ethylene glycol, triethyleneglyclol, glycerin, polyethyleneglycol, formic acid, acetic acid, formamide, acetone, tetrahydrofuran, dioxane, methyl ethyl ketone, high molecular weight ketones, ethyl acetate, acetonitrile, N,N-dimethylacetimide, dimethyl sulfoxide, carbon disulfide, hexane, hexane isomers, cyclohexane, heptane, heptane isomers, $C_8$-$C_{16}$ solvents, mineral oil, diethyl ether, methyl tert-butyl ether, methylene chloride, chloroform, carbon tetrachloride, benzene, nitrobenzene, toluene, and mixtures thereof.

5. A method according to claim 3, further comprising the step of separating the complex from the solution or suspension.

6. A method according to claim 5, wherein the step of separating the complex from the solution or suspension comprises isolation of the solid from the suspension or precipitation of the complex from the solution followed by isolation of the resulting solid.

7. A method according to claim 5, wherein the step of separating the complex from the solution or suspension comprises evaporation, or partial evaporation, of the solvent or solvents, followed by isolation of the resulting solid.

8. A method according to claim 5, wherein the step of separating the complex from the solution or suspension comprises saturating the solvent or solvents with cyclodextrin to decrease the solubility of the complex in the solvent or solvents.

9. A method according to claim 1, wherein the step of contacting sulforaphane, or an analog thereof, and at least one cyclodextrin comprises:
    dissolving or suspending the sulforaphane, or an analog thereof, in a solvent or mixture of solvents to form a solution or suspension; and
    dissolving or suspending the at least one cyclodextrin in the solution or suspension.

10. A method according to claim 9, wherein the solvent is selected from the group consisting of water, methanol, ethanol, n-propanol, iso-propanol, n-butanol, sec-butanol, iso-butanol, tert-butanol, high molecular weight alcohols, dimethyl formamide, diethyl formamide, ethylene glycol, triethyleneglyclol, glycerin, polyethyleneglycol, formic acid, acetic acid, formamide, acetone, tetrahydrofuran, dioxane, methyl ethyl ketone, high molecular weight ketones, ethyl acetate, acetonitrile, N,N-dimethylacetimide, dimethyl sulfoxide, carbon disulfide, hexane, hexane isomers, cyclohexane, heptane, heptane isomers, $C_8$-$C_{16}$ solvents, mineral oil, diethyl ether, methyl tert-butyl ether, methylene chloride, chloroform, carbon tetrachloride, benzene, nitrobenzene, toluene, and mixtures thereof.

11. A method according to claim 9, further comprising the step of separating the complex from the solution or suspension.

12. A method according to claim 11, wherein the step of separating the complex from the solution or suspension comprises isolation of the solid from the suspension or precipitation of the complex from the solution followed by isolation of the resulting solid.

13. A method according to claim 11, wherein the step of separating the complex from the solution or suspension comprises evaporation, or partial evaporation, of the solvent or solvents, followed by isolation of the resulting solid.

14. A method according to claim 11, wherein the step of separating the complex from the solution or suspension comprises saturating the solvent or solvents with cyclodextrin to decrease the solubility of the complex in the solvent or solvents.

15. A method according to claim 1, wherein the step of forming a complex between sulforaphane, or an analog thereof, and a cyclodextrin is conducted at room temperature.

16. A method according to claim 1, wherein the step of forming a complex between sulforaphane, or an analog thereof, and a cyclodextrin is conducted at a temperature above room temperature.

17. A method according to claim 1, wherein the step of forming a complex between sulforaphane, or an analog thereof, and a cyclodextrin is conducted at a temperature below room temperature.

18. A method according to claim 1, wherein the step of contacting sulforaphane, or an analog thereof, with at least one cyclodextrin to form a complex with cyclodextrin comprises contacting sufficient amounts of sulforaphane and a cyclodextrin to give a weight load of between about 0.01% wt/wt and about 30% wt/wt sulforaphane to cyclodextrin in the complex.

19. A method according to claim 1, wherein the step of contacting sulforaphane, or an analog thereof, and at least one cyclodextrin comprises:
    dissolving or suspending at least one cyclodextrin in a first solvent or mixture of solvents to form a first solution or suspension;
    dissolving or suspending sulforaphane, or an analog thereof, in a second solvent or mixture of solvents to form a second solution or suspension; and
    combining the first solution or suspension with the second solution or suspension.

20. A composition comprising a complex of sulforaphane and a cyclodextrin.

21. A composition according to claim 20, wherein said cyclodextrin is selected from the group consisting of W6 (alpha) cyclodextrin, W7 (beta) cyclodextrin, W8 (gamma) cyclodextrin, and mixtures thereof.

22. A composition comprising a complex of an analog of sulforaphane and a cyclodextrin, wherein the analog of sulforaphane is selected from the group consisting of 6-isothiocyanato-2-hexanone, exo-2-acetyl-6-isothiocyanatonorbornane, exo-2-isothiocyanoat-6-methylsulfonylnorbornane, 6-isothiocyanato-2-hexanol, 1-isothiocyanato-4-dimethylphosphonylbutane, exo-2-(1'-hydroxyethyl)-5-isothiocyanatonorborane, exo-2-acetyl-5-isothiocyanoatonorbornane, 1-isothiocyanato-5-methylsulfonylpentane, and cis- or trans-3-(methylsulfonyl)-cyclohexylmethyl-isothiocyanate, and mixtures thereof.

23. A composition according to claim 22, wherein said cyclodextrin is selected from the group consisting of W6 (alpha) cyclodextrin, W7 (beta) cyclodextrin, W8 (gamma) cyclodextrin, and mixtures thereof.

24. A pharmaceutical composition comprising a complex of cyclodextrin and sulforaphane, or an analog of sulforaphane selected from the group consisting of 6-isothiocyanato-2-hexanone, exo-2-acetyl-6-isothiocyanatonorbornane, exo-2-isothiocyanoat-6-methylsulfonylnorbornane, 6-isothiocyanato-2-hexanol, 1-isothiocyanato-4-dimethylphosphonylbutane, exo-2-(1'-hydroxyethyl)-5-isothiocyanatonorborane, exo-2-acetyl-5-isothiocyanoatonorbornane, 1-isothiocyanato-5-methylsulfonylpentane, and cis- or trans-3-(methylsulfonyl)-cyclohexylmethyl-isothiocyanate, and mixtures thereof, and an excipient.

25. A composition according to claim 24, wherein the cyclodextrin is selected from the group consisting of W6 (alpha) cyclodextrin, W7 (beta) cyclodextrin, W8 (gamma) cyclodextrin, and mixtures thereof.

26. A composition according to claim 24, wherein the excipient is suitable for one or more of oral, topical, parenteral, injectable, buccal, sublingual, intramuscular, or intravenous administration.

27. A composition according to claim 26, wherein the oral administration form is one or more of a dietary supplement, a food product, a food supplement, or a food additive.

28. A composition according to claim 26, wherein the topical administration form is one or more of a cream, jelly, ointment, or suspension.

29. A nutraceutical composition comprising a complex of cyclodextrin and sulforaphane, or an analog of sulforaphane one or more of 6 isothiocyanato-2-hexanone, exo-2-acetyl-6-isothiocyanatonorbornane, exo-2-isothiocyanato-6-methylsulfonylnorbornane, 6-isothiocyanato-2-hexanol, 1-isothiocyanato-4-dimethylphosphonylbutane, exo-2-(1'-hydroxyethyl)-5-isothiocyanatonorborane, exo-2-acetyl-5-isothiocyanoatonorbornane, 1-isothiocyanato-5-methylsulfonylpentane, and cis- or trans-3-(methylsulfonyl)-cyclohexylmethyl-isothiocyanate, and mixtures thereof, and an excipient.

30. A composition according to claim 29, wherein the cyclodextrin is selected from the group consisting of W6 (alpha) cyclodextrin, W7 (beta) cyclodextrin, W8 (gamma) cyclodextrin, and mixtures thereof.

31. A composition according to claim 29, wherein the excipient is suitable for one or more of oral, topical, parenteral, injectable, buccal, sublingual, intramuscular, or intravenous administration.

32. A composition according to claim 31, wherein the oral administration form is one or more of a dietary supplement, a food product, a food supplement, or a food additive.

33. A composition according to claim 31, wherein the topical administration form is one or more of a cream, jelly, ointment, or suspension.

* * * * *

UNITED STATES PATENT AND TRADEMARK OFFICE
CERTIFICATE OF CORRECTION

PATENT NO.         : 7,879,822 B2
APPLICATION NO.    : 12/009874
DATED              : February 1, 2011
INVENTOR(S)        : Ido Dov Dagan et al.

It is certified that error appears in the above-identified patent and that said Letters Patent is hereby corrected as shown below:

Column 5, line 17, replace the term "isothiocyanoatonorbormane" with the term
-- isothiocyanoatonorbornane --.

Signed and Sealed this
Twenty-sixth Day of April, 2011

David J. Kappos
*Director of the United States Patent and Trademark Office*